US012588681B2

(12) United States Patent
Lidor-Nili et al.

(10) Patent No.: US 12,588,681 B2
(45) Date of Patent: *Mar. 31, 2026

(54) COMPOSITIONS, KITS AND METHODS FOR WEED CONTROL

(71) Applicant: Weedout Ltd., Nes Ziona (IL)

(72) Inventors: Efrat Lidor-Nili, Nes Ziona (IL); Orly Noivirt-Brik, Givataim (IL)

(73) Assignee: Weedout Ltd., Nes Ziona (IL)

( * ) Notice: Subject to any disclaimer, the term of this patent is extended or adjusted under 35 U.S.C. 154(b) by 812 days.

This patent is subject to a terminal disclaimer.

(21) Appl. No.: 17/825,106

(22) Filed: May 26, 2022

(65) Prior Publication Data

US 2022/0279798 A1     Sep. 8, 2022

Related U.S. Application Data

(63) Continuation of application No. 16/304,145, filed as application No. PCT/IL2017/050568 on May 22, 2017, now Pat. No. 11,369,116.

(60) Provisional application No. 62/339,880, filed on May 22, 2016.

(51) Int. Cl.
| | |
|---|---|
| *A01N 65/08* | (2009.01) |
| *A01D 46/00* | (2006.01) |
| *A01H 1/06* | (2006.01) |
| *C12N 15/82* | (2006.01) |

(52) U.S. Cl.
CPC .............. *A01N 65/08* (2013.01); *A01H 1/06* (2013.01); *C12N 15/8218* (2013.01); *C12N 15/8287* (2013.01); *A01D 46/00* (2013.01)

(58) Field of Classification Search
None
See application file for complete search history.

(56) References Cited

U.S. PATENT DOCUMENTS

| | | |
|---|---|---|
| 8,437,498 B2 | 5/2013 | Malsam |
| 11,369,116 B2 | 6/2022 | Lidor-Nili et al. |
| 11,812,735 B2 | 11/2023 | Lidor-Nili et al. |
| 11,957,097 B2 | 4/2024 | Shwartz et al. |
| 2006/0053686 A1 | 3/2006 | Halwas |
| 2017/0042102 A1 | 2/2017 | Safreno |
| 2017/0359943 A1 | 12/2017 | Calleija et al. |
| 2018/0065749 A1 | 3/2018 | Cantrell |
| 2019/0208790 A1 | 7/2019 | Lidor-Nili et al. |
| 2020/0275617 A1 | 9/2020 | Fabijanski et al. |
| 2020/0281139 A1 | 9/2020 | Noivirt-Brik et al. |
| 2020/0288656 A1 | 9/2020 | Lidor-Nili et al. |
| 2020/0288657 A1 | 9/2020 | Novirt-Brik et al. |
| 2021/0068335 A1 | 3/2021 | Noivirt-Brik et al. |
| 2021/0127610 A1 | 5/2021 | Lidor-Nili et al. |
| 2021/0315176 A1 | 10/2021 | Shwartz et al. |
| 2024/0057586 A1 | 2/2024 | Lidor-Nili et al. |
| 2024/0268289 A1 | 8/2024 | Shwartz |

FOREIGN PATENT DOCUMENTS

| | | |
|---|---|---|
| CN | 1395823 | 2/2003 |
| CN | 101536671 | 9/2009 |
| CN | 102106253 | 6/2011 |
| CN | 103782902 | 5/2014 |
| FR | 2933842 | 1/2010 |
| WO | WO 2014/085774 | 6/2014 |
| WO | WO 2015/164805 | 10/2015 |
| WO | WO 2016/191825 | 12/2016 |
| WO | WO 2017/194399 | 11/2017 |
| WO | WO 2017/203519 | 11/2017 |
| WO | WO 2007/093444 | 7/2018 |
| WO | WO 2019/106666 | 6/2019 |
| WO | WO 2019/106667 | 6/2019 |
| WO | WO 2019/106668 | 6/2019 |
| WO | WO 2019/215581 | 11/2019 |
| WO | WO 2019/215582 | 11/2019 |
| WO | WO 2020/084586 | 4/2020 |
| WO | WO 2020/084586 A9 | 10/2020 |

OTHER PUBLICATIONS

Behera et al 1975, Cytologia 40: 157-168 (Year: 1975).*
Milan 2008, Caryologia 61(3): 199-205 (Year: 2008).*
Hricova et al 2016, Turkish Journal of Agriculture and Forestry 40: 761-771 (Year: 2016).*
Wu et al 2024, Weed Science 72: 234-240 (Year: 2024).*
Rector 2009, Pest Management Science 65: 596-602 (Year: 2009).*
Hearing Notice Dated Jul. 3, 2023 From the Government of India, Intellectual Property India, The Patent Office Re. Application No. 201827046713. (2 Pages).
Relatório de Busca e Parecer Dated Mar. 11, 2025 From the Serviço Público Federal, Ministério da Economia, Instituto Nacional da Propriedade Industrial do Brasil Re. Application No. BR 11 2020 010830 8 and Its Translation Into English. (7 Pages).
Requisition by the Examiner Dated Jun. 9, 2023 From the Innovation, Science and Economic Development Canada, Canadian Intellectual Property Office Re. Application No. 3,024,079. (6 Pages).
Translation Dated Jun. 17, 2023 of Decision on Rejection Dated May 29, 2023 From the State Intellectual Property Office of the People's Republic of China Re. Application No. 201880086827.5. (3 pages).
Official Action Dated Jun. 6, 2024 from the US Patent and Trademark Office Re. U.S. Appl. No. 16/884,362. (12 pages).
Final Official Action Dated Jun. 30, 2022 from US Patent and Trademark Office Re. U.S. Appl. No. 16/885,311. (30 pages).
Notification of Office Action Dated Jun. 24, 2022 From the State Intellectual Property Office of the People's Republic of China Re. Application No. 201780037868.0 and Its Translation Into English. (10 Pages).

(Continued)

*Primary Examiner* — Shubo Zhou
*Assistant Examiner* — Aleksandar Radosavljevic

(57) ABSTRACT

A method of weed control is provided. The method comprises artificially pollinating at least one weed species of interest with pollen of the same species that reduces fitness of said at least one weed species of interest. Also provided are compositions and kits which can be used for performing the methods described herein.

3 Claims, 3 Drawing Sheets

(56)                    References Cited

OTHER PUBLICATIONS

Interview Summary Dated Oct. 20, 2023 from the US Patent and Trademark Office Re. U.S. Appl. No. 17/287,574. (3 pages).
Final Official Action Dated Jun. 22, 2022 from US Patent and Trademark Office Re. U.S. Appl. No. 16/884,362. (32 pages).
Communication Pursuant to Article 94(3) EPC Dated Sep. 25, 2024 From the European Patent Office Re. Application No. 18883157.2 (5 Pages).
Office Action Dated Feb. 28, 2023 From the Israel Patent Office Re. Application No. 274978. (3 Pages).
Notice of Allowance Dated Jul. 6, 2023 from the US Patent and Trademark Office Re. U.S. Appl. No. 17/052,834. (18 pages).
Official Action Dated May 23, 2023 from the US Patent and Trademark Office Re. U.S. Appl. No. 16/884,362. (20 pages).
Brewbaker et al. "Pollen Radiobotany", Radiation Botany, 1: 101-154, 1962.
Communication Pursuant to Article 94(3) EPC Dated Jul. 20, 2023 From the European Patent Office Re. Application No. 18883157.2 (5 Pages).
Notice of Allowance Dated Dec. 13, 2023 from the US Patent and Trademark Office Re. U.S. Appl. No. 17/287,574. (17 pages).
Official Action Dated Dec. 7, 2023 from the US Patent and Trademark Office Re. U.S. Appl. No. 16/884,362. (23 pages).
Official Action Dated Dec. 7, 2023 from the US Patent and Trademark Office Re. U.S. Appl. No. 16/885,311. (23 pages).
Ward et al. "Palmer Amaranth (Amaranthus Palmeri): A Review", Weed Technology, 27: 12-27, Jan.-Mar. 2013.
Official Action Dated Apr. 30, 2024 from the US Patent and Trademark Office Re. U.S. Appl. No. 18/385,412. (25 pages).
Communication Pursuant to Article 94(3) EPC Dated Aug. 28, 2024 From the European Patent Office Re. Application No. 17802323.0. (4 Pages).
Notice of Allowance Dated Aug. 30, 2024 from the US Patent and Trademark Office Re. U.S. Appl. No. 18/385,412. (9 pages).
Requisition by the Examiner Dated Sep. 5, 2024 From the Innovation, Science and Economic Development Canada Re. Application No. 3,024,079. (3 Pages).
Examination Report Dated Jan. 27, 2023 From the Australian Government, IP Australia Re. Application No. 2017271409. (5 Pages).
Notification of Office Action Dated Jan. 9, 2023 From the State Intellectual Property Office of the People's Republic of China Re. Application No. 201780037868.0. (4 Pages).
Notification of Office Action Dated Dec. 28, 2022 From the China National Intellectual Property Administration Re. Application No. 201880086827.5. (5 Pages).
Translation Dated Jan. 13, 2023 of Notification of Office Action Dated Dec. 28, 2022 From the China National Property Administration Re. Application No. 201880086827.5. (3 Pages).
Translation Dated Jan. 19, 2023 of Notification of Office Action Dated Jan. 9, 2023 From the State Intellectual Property Office of the People's Republic of China Re. Application No. 201780037868.0. (6 Pages).
Communication Pursuant to Article 94(3) EPC Dated Dec. 2, 2022 From the European Patent Office Re. Application No. 17802323.0 with Claims. (7 Pages).
Notice of Allowance Dated Nov. 22, 2024 from the US Patent and Trademark Office Re. U.S. Appl. No. 16/884,362. (11 pages).
Requisition by the Examiner Dated Apr. 8, 2025 From the Innovation, Science and Economic Development Canada, Canadian Intellectual Property Office Re. Application No. 3,083,436. (7 Pages).
Official Action Dated Feb. 9, 2023 from US Patent and Trademark Office Re. U.S. Appl. No. 17/052,834. (25 pages).
Andreichenko et al. "Possibility of Regulating Seed Formation During Pollination with Mixed Pollen Containing γ-irradiated Pollen", A. A. Bogomolets Kiev Medical Institute, Kiev, Doklady, Biological Sciences, 315(1-6): 699-702, ref. 15, Dec. 1990.

Feng et al. "Effect of Enhanced Ultraviolet-B Radiation on Pollen Germination and Tube Growth of 19 Taxa in Vitro", Environmental and Experimental Botany, 43(1):45-53, Feb. 2000.
Hansen "Precision Pollination. Mechanical Pollination Could end Use of Chemicals or Hand Labor for Thinning." Retrieved from The Internet: www.goodfruit.com, 4 pages, Mar. 18, 2015.
Advisory Action Dated Mar. 1, 2022 From the US Patent and Trademark Office Re. U.S. Appl. No. 16/884,097. (11 Pages).
Clarifications Prior to Substantive Examination Dated Nov. 18, 2021 From the Instituto Nacional De La Propiedad Industrial Administracion Nacional De Patentes Argentina Re. Applicatiion No. P20170101373 together with English Summary. (6 Pages).
Communication Pursuant to Article 94(3) EPC Dated Aug. 12, 2021 From the European Patent Office Re. Application No. 17802323.0. (7 Pages).
Communication Pursuant to Article 94(3) EPC Dated Nov. 20, 2020 From the European Patent Office Re. Application No. 17802323.0. (5 Pages).
English Translation Dated Apr. 6, 2022 of Notification of Office Action and Search Report Dated Mar. 10, 2022 From the State Intellectual Property Office of the People's Republic of China Re. Application No. 201880086827.5. (4 Pages).
English Translation of Notification of Office Action Dated Jan. 25, 2022 From the State Intellectual Property Office of the People's Republic of China Re. Application No. 201780037868.0. (5 Pages).
Examination Report Under Sections 12 & 13 of the Patents Act, 1970 and the Patents Rules, 2003 Dated Jul. 16, 2021 From the Government of India, Intellectual Property India, Patents, Designs, Trade Marks, Geographical Indications, The Patent Office Re. Application No. 201827046713. (7 Pages).
Final Official Action Dated Nov. 3, 2021 from the US Patent and Trademark Office Re. U.S. Appl. No. 16/884,097. (36 pages).
Final Official Action Dated Sep. 16, 2021 from the US Patent and Trademark Office Re. U.S. Appl. No. 16/304,145. (32 pages).
Final Official Action Dated Jul. 21, 2021 from the US Patent and Trademark Office Re. U.S. Appl. No. 17/053,089. (34 pages).
International Preliminary Report on Patentability Dated Dec. 6, 2018 From the International Bureau of WIPO Re. Application No. PCT/IL2017/050568. (8 Pages).
International Preliminary Report on Patentability Dated May 6, 2021 From the International Bureau of WIPO Re. Application No. PCT/IB2019/059171. (7 Pages).
International Preliminary Report on Patentability Dated Jun. 11, 2020 From the International Bureau of WIPO Re. Application No. PCT/IL2018/051301. (8 Pages).
International Preliminary Report on Patentability Dated Jun. 11, 2020 From the International Bureau of WIPO Re. Application No. PCT/IL2018/051302. (7 Pages).
International Preliminary Report on Patentability Dated Jun. 11, 2020 From the International Bureau of WIPO Re. Application No. PCT/IL2018/051303. (8 Pages).
International Preliminary Report on Patentability Dated Nov. 19, 2020 From the International Bureau of WIPO Re. Application No. PCT/IB2019/053688. (7 Pages).
International Search Report and the Written Opinion Dated Dec. 12, 2019 From the International Searching Authority Re. Application No. PCT/IB2019/059171. (9 Pages).
International Search Report and the Written Opinion Dated Aug. 14, 2019 From the International Searching Authority Re. Application No. PCT/TB2019/053690. (13 Pages).
International Search Report and the Written Opinion Dated Jul. 14, 2019 From the International Searching Authority Re. Application No. PCT/IB2019/053688. (10 Pages).
International Search Report and the Written Opinion Dated Feb. 21, 2019 From the International Searching Authority Re. Application No. PCT/IL2018/051301. (11 Pages).
International Search Report and the Written Opinion Dated Aug. 23, 2017 From the International Searching Authority Re. Application No. PCT/IL2017/050568. (11 Pages).
International Search Report and the Written Opinion Dated Feb. 24, 2019 From the International Searching Authority Re. Application No. PCT/IL2018/051302. (9 Pages).

(56) References Cited

OTHER PUBLICATIONS

International Search Report and the Written Opinion Dated Feb. 26, 2019 From the International Searching Authority Re. Application No. PCT/IL2018/051303. (11 Pages).

Interview Summary Dated Dec. 13, 2021 from US Patent and Trademark Office Re. U.S. Appl. No. 16/304,145. (2 pages).

Notice of Allowance Dated Feb. 9, 2022 from US Patent and Trademark Office Re. U.S. Appl. No. 16/304,145. (7 pages).

Notice of Allowance Dated Dec. 21, 2021 from US Patent and Trademark Office Re. U.S. Appl. No. 17/053,089. (12 pages).

Notification of Office Action and Search Report Dated Mar. 10, 2022 From the State Intellectual Property Office of the People's Republic of China Re. Application No. 201880086827.5. (25 Pages).

Notification of Office Action Dated Jul. 2, 2021 From the State Intellectual Property Office of the People's Republic of China Re. Application No. 201780037868.0 and Its English Summary. (6 Pages).

Notification of Office Action Dated Jan. 25, 2022 From the State Intellectual Property Office of the People's Republic of China Re. Application No. 201780037868.0 with an English Summry. (6 Pages).

Office Action Dated Jul. 9, 2019 From the Israel Patent Office Re. Application No. 263232 and Its Translation Into English. (5 Pages).

Office Action Dated Dec. 10, 2020 From the Israel Patent Office Re. Application No. 263232 and Its Translation Into English. (9 Pages).

Office Action Dated Mar. 31, 2022 From the Israel Patent Office Re. Application No. 263232 and Its Translation Into English. (6 Pages).

Official Action Dated Feb. 2, 2021 From the US Patent and Trademark Office Re. U.S. Appl. No. 16/884,097. (36 Pages).

Official Action Dated Feb. 17, 2021 From the US Patent and Trademark Office Re. U.S. Appl. No. 17/053,089. (45 Pages).

Official Action Dated Nov. 18, 2021 from the US Patent and Trademark Office Re. U.S. Appl. No. 16/884,362 (56 pages).

Official Action Dated Nov. 18, 2021 from the US Patent and Trademark Office Re. U.S. Appl. No. 16/885,311. (55 pages).

Official Action Dated Dec. 30, 2020 from the US Patent and Trademark Office Re. U.S. Appl. No. 16/304,145. (37 pages).

Restriction Official Action Dated Aug. 2, 2021 from the US Patent and Trademark Office Re. U.S. Appl. No. 16/885,311. (8 pages).

Restriction Official Action Dated May 3, 2022 from US Patent and Trademark Office Re. U.S. Appl. No. 17/052,834. (6 pages).

Restriction Official Action Dated Oct. 1, 2020 from the US Patent and Trademark Office Re. U.S. Appl. No. 16/304,145. (9 pages).

Restriction Official Action Dated Jul. 12, 2021 from the US Patent and Trademark Office Re. U.S. Appl. No. 16/884,362. (8 pages).

Supplementary European Search Report and the European Search Opinion Dated Aug. 13, 2021 From the European Patent Office Re. Application No. 18883157.2 (120 Pages).

Supplementary European Search Report and the European Search Opinion Dated Aug. 13, 2021 From the European Patent Office Re. Application No. 18883823.9. (8 Pages).

Supplementary European Search Report and the European Search Opinion Dated Oct. 25, 2019 From the European Patent Office Re. Application No. 17802323.0. (9 Pages).

Translation Dated Jul. 14, 2021 of Notification of Office Action Dated Jul. 2, 2021 From the State Intellectual Property Office of the People's Republic of China Re. Application No. 200880024068. (6 Pages).

Translation Dated Jul. 14, 2021 of Notification of Office Action Dated Jul. 2, 2021 From the State Intellectual Property Office of the People's Republic of China Re. Application No. 201780037868.0. (6 Pages).

Al-Ahmad et al. "Mitigation of Establishment of *Brassica napus* Transgenes in Volunteers Using A Tandem Construct Containing A Selectively Unfit Gene", Plant Biotechnology Journal, XP055444715, 4(1): 7-21, Jan. 2006. Abstract, p. 16, r-h col., 1st Para, p. 17, 1-h col., 4th Para.

Al-Ahmad et al. "Mitigation Using A Tandem Construct Containing A Selectively Unfit Gene Precludes Establishment of *Brassica napus* Transgenes in Hybrids and Backcrosses With Weedy Brassica Rapa", Plant Biotechnology Journal, XP055444720, 4(1): 23-33, Published Online Aug. 16, 2005. Abstract, Table S2, p. 31, 1-h col., Lines 10-11, 18-23.

Bae et al. "Production of Unbolting Lines Through Gamma-Ray Irradiation Mutagenesis in Genetically Modified Herbicide-Tolerant Zoysia Japonica", Breeding Science, 59(1): 103-105, 2009.

Chin et al. "Pollination With Irradiated Pollen in Rice—*Oryza sativa* L. I. First (M1) Generation", Heredity, 63(2): 163-170, Published Online Oct. 1, 1989.

Culpepper et al. "Glyphosate-Resistant Palmer Amaranth (Amaranthus Palmeri) Confirmed in Georgia", Weed Science, 54(4):620-626, Jul. 1, 2006.

Daher et al. "Optimization of Conditions for Germination of Cold-Stored *Arabidopsis thaliana* Pollen", Plant Cell Reports, 28: 347-357, 2009.

Germana "Use of Irradiated Pollen to Induce Parthenogenesis and Haploid Production in Fruit Crops", Plant Mutation Breeding and Biotechnology, XP009516584, p. 411-415, Published Online Dec. 31, 2012.

Gressel et al. "A Strategy to Provide Long-Term Control of Weedy Rice While Mitigating Herbicide Resistance Transgene Flow, and Its Potential Use for Other Crops With Related Weeds", Pest Management Science, XP055053395, 65(7): 723-731, Published Online Apr. 14, 2009.

He "Garden Plant Breeding", China Forestry Publishing House: 174-189, Aug. 1992. Chinese Document only).

Jordan et al. "Biorational Management Tactics to Select Against Triazine-Resistant Amaranthus Hybridus: A Field Trial", Journal of Applied Ecology, 36(1): 123-132, Feb. 1999.

Keller et al. "Genetic Introgression From Distant Provenances Reduces Fitness in Local Weed Populations", Journal of Applied Ecology, 37(4): 647-659, Aug. 2000.

Kosmrlj et al. "Haploid Induction in Hull-less Seed Pumpkin through Parthenogenesis Induced by X-ray-irradiated Pollen". Journal of the American Society for Horticultural Science. 138(4):310-316.(Year:2013).

Kurtar "Influence of Gamma Irradiation on Pollen Viability, Germination Ability, and Fruit and Seed-Set of Pumpkin and Winter Squash", African Journal of Biotechnology, 8(24): 6918-6926, Dec. 15, 2009.

Kwit et al. "Transgene Introgression in Crop Relatives: Molecular Evidence and Mitigation Strategies", Trends in Biotechnology, XP002794936, 29(6): 284-293, Published Online Mar. 8, 2011.

Lagera et al. "Varying Sugars and Sugar Concentrations Influence In Vitro Pollen Germination and Pollen Tube Growth of *Cassia alata* L.", Journal of Young Investigations, 33(1): 42-45, Jun. 2017.

Li et al. "Effects of Sowing Date on Phenotypic Plasticity of Fitness-Related Traits in Two Annual Weeds on the Songnen Plain of China", PLOS ONE, 10(5): e0127795-1-0127795-15, May 29, 2005.

Ma "Why Don't They Genetically Modify Weeds Instead fo Crops? Wouldn't It Make More Sense to Genetically Alter Species of Weeds to Become Interfile After A Few Generations, Thereby Reducing the Need for Herbicides?", Quora.com, 1 P., Apr. 2, 2014.

Munusamy et al. "Female Reproductive System of Amaranthus as the Target for Agrobacterium-Mediated Transformation", Advances in Biscience and Biotechnology, 4(2): 188-192, Published Online Feb. 28, 2013.

Murphy "The Role of Pollen Allelopathy in Weed Ecology", Weed Technology, 15(4):867-872, Dec. 2001.

Peixe et al. "Gamma-Irradiated Pollen Induces the Formation of 2n Endosperm and Abnormal Embryo Development in European Plum (*Prunus domestica* L., Cv. 'Rainha Claudia Verde')", Scientia Horticulturae, 86(4): 267-278, Dec. 2000.

Preston et al. "A Decade of Glyphosate-Resistant Lolium around the World: Mechanisms, Genes, Fitness, and Agronomic Management", Weed Science, 57(4):435-441, Jul. 1, 2009.

Shu "Use of Irradiated Pollen to Induce Pathogenesis and Haploid Production in Fruit Crops", Plant Mutation Breeding and Biotechnology, C30: 412-416, Dec. 2012.

Tacconi et al. "Kiwifruit Pollination: the Interaction Between Pollen Quality, Pollination Systems and Flowering Stage", Journal of Berry Research, 6(4): 417-426, Dec. 12, 2016.

(56)                References Cited

OTHER PUBLICATIONS

Yang et al. "Molecular Genetic Analysis of Pollen Irradiation Mutagenesis in *Arabidopsis*", New Phytologist, XP055615348, 164(2): 279-288, Published Online Sep. 10, 2004.

Official Action Dated May 24, 2023 From the US Patent and Trademark Office Re. U.S. Appl. No. 17/287,574. (106 Pages).

Marcelis et al. "Flower and Fruit Abortion in Sweet Pepper in Relation to Source and Sink Strength", Journal of Experimental Botany, 55(406): 2261-2268, Oct. 2004.

Muthoni et al. "Reproductive Biology and Early Generation's Selection in Conventional Potato Breeding", Australian Journal of Crop Science, 6(3): 488-497, Mar. 2012.

Ribeiro et al. "Involvement of Facultative Apomixis in Inheritance of EPSPS Gene Amplification in Glyphosate-resistant Amaranthus Palmeri", Planta, 239: 199-212, 2014.

Spaunhorst et al. "Phenology of Five Palmer Amaranth (Amaranthus palmcri) Populations Grown in Northern Indiana and Arkansas", Weed Science 66(4): 457-469, Mar. 27, 2018.

Decision on Rejection Dated May 29, 2023 From the State Intellectual Property Office of the People's Republic of China Re. Application No. 201880086827.5. (4 Pages).

Requisition by the Examiner Dated May 22, 2024 From the Innovation, Science and Economic Development Canada, Canadian Intellectual Property Office Re. Application No. 3,100,078. (3 Pages).

Restriction Official Action Dated Nov. 15, 2022 from the US Patent and Trademark Office Re. U.S. Appl. No. 17/287,574. (14 pages).

Yang et al. "Molecular Genetic analysis of Pollen Irradiation Mutagenesis in *Arabidopsis*", New Phytologist, 164(2): 279-288, Sep. 10, 2004.

Official Action Dated Sep. 9, 2022 from US Patent and Trademark Office Re. U.S. Appl. No. 17/052,834. (65 pages).

Relatório de Busca e Parecer [Search Report and Written Opinion] Dated Sep. 19, 2022 From the Serviço Público Federal, Ministério da Economia, Instituto Nacional da Propriedade Industrial do Brasil Re. Application No. BR112018074045-4 and Its Summary of Written Opinion in English. (6 Pages).

Communication Pursuant to Article 94(3) EPC Dated Sep. 4, 2025 From the European Patent Office Re. Application No. 18883157.2. (5 Pages).

Examination Report Dated Sep. 4, 2025 From the Servico Publico Federal, Ministerio da Economia, Instituto Nacional da Propriedade Industrial do Brasil RE Application No. BR112018074045.4 and Its Machine Translation into English. (10 Pages).

Relatório de Exame Tecnico Dated May 27, 2025 From the Serviço Público Federal, Ministério da Economia, Instituto Nacional da Propriedade Industrial do Brasil Re. Application No. BR 11 2018 074045 4 and Its Translation Into English. (13 Pages).

Notification of Reexamination Dated Feb. 5, 2026 From the State Intellectual Property Office of the People's Republic of China Re. Application No. 201780037868.0 and Its Machine Translation Into English. (13 Pages).

\* cited by examiner

| | |
|---|---|
| Regular pollen 1 | |
| Regular pollen 2 | |
| Regular pollen 3 | |
| Regular pollen 4 | |
| X-Ray 300Gy 1 | |
| X-Ray 300Gy 2 | |
| X-Ray 300Gy 3 | |
| X-Ray 300Gy 4 | |

| Regular pollen 1 |
| Regular pollen 2 |
| X-Ray 300Gy 1 |
| X-Ray 300Gy 2 |

| Regular pollen 1 | | Gamma 300Gy 1 | |
| Regular pollen 2 | | Gamma 300Gy 2 | |
| Regular pollen 3 | | Gamma 300Gy 3 | |
| Regular pollen 4 | | Gamma 300Gy 4 | |
| Gamma 100Gy 1 | | Gamma 500Gy 1 | |
| Gamma 100Gy 2 | | Gamma 500Gy 2 | |
| Gamma 100Gy 3 | | Gamma 500Gy 3 | |
| Gamma 100Gy 4 | | Gamma 500Gy 4 | |

COMPOSITIONS, KITS AND METHODS FOR WEED CONTROL

RELATED APPLICATIONS

This application is a continuation of U.S. patent application Ser. No. 16/304,145, filed on Nov. 22, 2018, which is a National Phase of PCT Patent Application No. PCT/IL2017/050568 having International Filing Date of May 22, 2017, which claims the benefit of priority under 35 USC § 119(e) of U.S. Provisional Patent Application No. 62/339,880 filed on May 22, 2016. The contents of the above applications are all incorporated by reference as if fully set forth herein in their entirety.

FIELD AND BACKGROUND OF THE INVENTION

The present invention, in some embodiments thereof, relates to compositions, kits and methods for weed control.

Weeds have been the major biotic cause of crop yield loses since the origins of agriculture. The potential of weed damages is estimated as 34% loss of crop yield, on average, world-wide [Oerke, E-C., 2006]. In the USA alone, the annual cost of crop losses due to weeds is greater than 26 billion USD [Pimentel D et al., 2000]. Furthermore according to the Weed Science Society of America Weeds are estimated to billion in cause more than 40 USD annual global losses [wssa(dot)net/wssa/weed/biological-control/]. Weeds are thus a major threat to food security [Delye et al., 2013].

Herbicides are the most commonly used and effective weed control tools. Due to the intense selection pressure exerted by herbicides, herbicide resistance is constantly growing and as of 2016 there are over 470 weed biotypes currently identified as being herbicide resistant to one or more herbicides by The International Survey of Herbicide Resistant Weeds (weedscience (dot) org/).

Weeds, like other plants, have several sexual reproduction mechanisms: self-pollination, cross-pollination, or both. Self-pollination describes pollination using pollen from one flower that is transferred to the same or another flower of the same plant. Cross-pollination describes pollination using pollen delivered from a flower of a different plant. Weeds rely on wind, or animals such as bees and other insects to pollinate them.

Since the 1940's the use of sterile organisms has been reported for use in order to reduce pest population and the success of these methods was demonstrated in many cases such as the tsetse fly [Klassen& Curtis, 2005], melon fly [Yosiaki et al. 2003] and Sweet potato weevil [Kohama et al., 2003].

Planting in the field plants producing sterile pollen for the production of infertile seeds was mentioned but immediately over-ruled due to practical, regulatory and economic reasons. (quora (dot) com/Why-dont-they-genetically-modify-weeds-instead-of-crops).

Therefore, there still exists a need for biological weed control.

SUMMARY OF THE INVENTION

According to an aspect of some embodiments of the present invention there is provided a method of weed control, the method comprising artificially pollinating at least one weed species of interest with pollen of the same species that reduces fitness of the at least one weed species of interest.

According to some embodiments of the invention, the artificially pollinating is effected in a large scale setting.

According to some embodiments of the invention, the weed species of interest is a herbicide resistant weed.

According to some embodiments of the invention, the method further comprises treating the at least one weed species of interest with a herbicide.

According to some embodiments of the invention, the treating is prior to the pollinating.

According to an aspect of some embodiments of the present invention there is provided a method of producing pollen, the method comprising:

(a) growing weed producing pollen that reduces fitness of at least one weed species of interest; and (b) harvesting the pollen.

According to an aspect of some embodiments of the present invention there is provided a method of producing pollen that reduces fitness of at least one weed species of interest, the method comprising treating the weed species of interest or pollen thereof with an agent that reduces fitness.

According to some embodiments of the invention, the method comprises harvesting pollen from the weed species of interest prior to or following the treating.

According to some embodiments of the invention, the agent that reduces fitness of the at least one weed species of interest is selected from the group consisting of a polyploidy inducing agent and a mutagenizing agent.

According to some embodiments of the invention, the mutagenizing agent is radiation.

According to some embodiments of the invention, the radiation is selected from the group of X-ray radiation, gamma radiation and UV radiation.

According to some embodiments of the invention, the weed producing pollen comprise only male plants.

According to some embodiments of the invention, the growing the weed producing pollen that reduces fitness is effected in a large scale setting.

According to some embodiments of the invention, the large scale setting essentially does not comprise crops.

According to an aspect of some embodiments of the present invention there is provided a method of producing pollen for use in artificial pollination, the method comprising:

(a) obtaining pollen that reduces fitness of at least one weed species of interest; and (b) treating the pollen for use in artificial pollination.

According to some embodiments of the invention, the obtaining is effected according to the method as described herein.

According to an aspect of some embodiments of the present invention there is provided a composition-of-matter comprising weed pollen that reduces fitness of at least one weed species of interest, the pollen having been treated for use in artificial pollination.

According to an aspect of some embodiments of the present invention there is provided a kit comprising a plurality of packaging means, each packaging different species of pollen that reduce fitness of weed species of interest, the pollen having been treated for use in artificial pollination.

According to an aspect of some embodiments of the present invention there is provided a kit comprising a plurality of packaging means, wherein a first packaging means packaging at least one species of pollen that reduce fitness of weed species of interest and a second another packaging means separately packaging a chemical inducer for affecting gene expression in the pollen.

According to some embodiments of the invention, a treatment of the treated pollen is selected from the group consisting of coating, priming, formulating, solvent solubilizing, chemical treatment, drying, heating, cooling and irradiating.

According to some embodiments of the invention, the chemical treatment comprises a chemical inducer.

According to some embodiments of the invention, the chemical inducer is selected from the group consisting of an antibiotic, a hormone, a steroid, a herbicide, a pesticide, alcohol and a metal.

According to some embodiments of the invention, the antibiotic comprises tetracycline or a tetracycline derivative.

According to some embodiments of the invention, the weed species of interest is selected from the group consisting of a biotic stress or abiotic stress resistant weed.

According to some embodiments of the invention, the weed species of interest is a herbicide resistant weed.

According to some embodiments of the invention, the pollen is of an herbicide susceptible weed.

According to some embodiments of the invention, the herbicide susceptible weed is susceptible to a plurality of herbicides.

According to some embodiments of the invention, the pollen reduces productiveness of the weed species of interest.

According to some embodiments of the invention, reduction in the productiveness is manifested by:
  (i) inability to develop an embryo;
  (ii) embryo abortion;
  (iii) seed non-viability;
  (iv) seed that cannot fully develop;
  (v) seed that is unable to germinate; and/or
  (vi) reduced or no seed set.

According to some embodiments of the invention, the pollen is non-genetically modified pollen.

According to some embodiments of the invention, the non-genetically modified pollen is produced from a plant selected from the group consisting of having an imbalanced chromosome number as compared to the weed species of interest, naturally occurring plant exhibiting reduced fitness and selected for reduced fitness with or without a mutagen.

According to some embodiments of the invention, the non-genetically modified pollen is irradiated pollen.

According to some embodiments of the invention, the pollen is genetically modified pollen.

According to some embodiments of the invention, the pollen is modified by a methodology selected from the group consisting of Genetic Use Restriction Technology, reversed methodology, dual complementary male and female plant genetic recombination system, chemical or physical inducible system, antisense based system, cytoplasmic male sterility methodology and genome editing.

According to some embodiments of the invention, the weed species of interest is an annual weed.

According to some embodiments of the invention, the weed species of interest is a perennial weed.

According to some embodiments of the invention, the weed species of interest is a biennial weed.

According to some embodiments of the invention, the weed species of interest is selected from the group consisting of *Amaranthus: A. palmeri, A. tuberculatus, Lolium rigidum, Ambrosia: A. trifida, A. artemisiifolia, Kochia scoparia, Conyza: C. canadensis, C. bonariensis, Echi-*

*nochloa, Alopecurus myosuroides, Sorghum halepense, Digitaria insularis, Eleusine indica, Avena fatua, Euphorbia Heterophylla, Chenopodium album.*

According to some embodiments of the invention, the composition or kit further comprises at least one agent selected from the group consisting of an agricultural acceptable carrier, a fertilizer, a herbicide, an insecticide, a miticide, a fungicide, a pesticide, a growth regulator, a chemosterilant, a semiochemical, a pheromone and a feeding stimulant.

According to some embodiments of the invention, the at least one weed species of interest comprises a plurality of weed species of interest and the pollen is of species of the plurality of weed species.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 5:
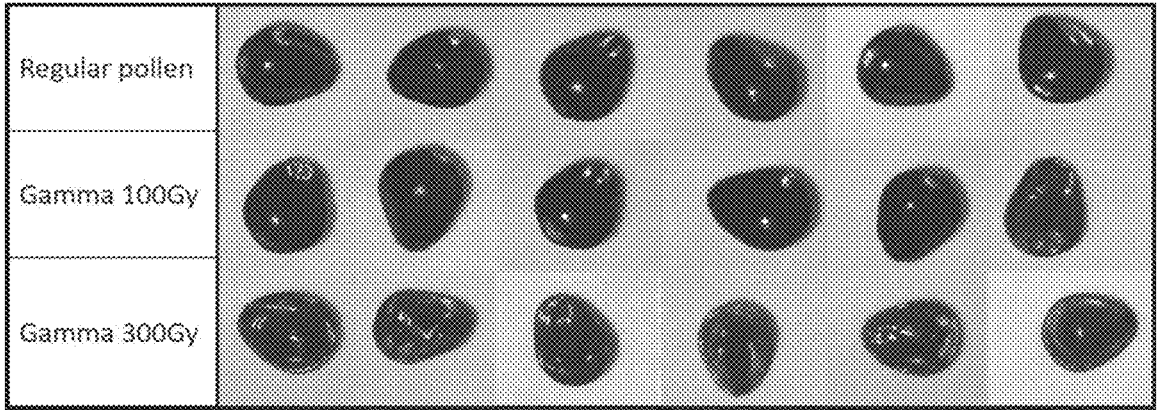

FIG. 5 an image showing inhibition of seed development demonstrated by comparing the appearance of random assortment of seeds generated by artificial pollination with gamma irradiated pollen vs. non-irradiated pollen. A dose response is demonstrated.

DESCRIPTION OF SPECIFIC EMBODIMENTS OF THE INVENTION

The present invention, in some embodiments thereof, relates to compositions, kits and methods for weed control.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Weeds are plants that are unwanted in any particular environment. They compete with cultivated plants in an agronomic environment and also serve as hosts for crop diseases and insect pests. The losses caused by weeds in agricultural production environments include decreases in crop yield, reduced crop quality, increased irrigation costs, increased harvesting costs, reduced land value, injury to livestock, and crop damage from insects and diseases harbored by the weeds.

The use of herbicides and other chemicals to control weed has generated environmental concern.

Whilst conceiving the present invention, the present inventors have devised a novel approach for the biological control of weeds. The approach is based on producing weed pollen that when artificially applied to the invasive weed out-competes with native fertilization and causes reduction in fitness of the weed. Thus, the present teachings provide for products and methods which are highly efficient, environmentally safe and that can be successfully applied as a practical and economically affordable weed control in plethora of settings.

Thus, according to an aspect of the invention there is provided a method of weed control. The method comprises artificially pollinating at least one weed species of interest with pollen of the same species that reduces fitness of the at least one weed species of interest.

As used herein the term "weed species of interest" refers to a wild plant growing where it is not wanted and that may be in competition with cultivated plants of interest (i.e., crop-desirable plants). Weeds are typically characterized by rapid growth and/or ease of germination, and/or competition with crops for space, light, water and nutrients. According to some embodiments of the invention, the weed species of interest is traditionally non-cultivated.

According to another embodiment of the invention, the weed is a perennial weed.

According to another embodiment of the invention the weed is a biennial weed.

According to another embodiment of the invention the weed is an annual weed.

According to another embodiment of the invention the weed is a therophyte.

According to an embodiment, the weed is a parasitic plant.

Examples of weed species which can be targeted (mitigated) according to the present teachings include, but are not limited to, *Amaranthus* species—*A. albus, A. blitoides, A. hybridus, A. palmeri, A. powellii, A. retroflexus, A. rudis, A. spinosus, A. tuberculatus*, and *A. viridis; Ambrosia* species—*A. trifida, A. artemisifolia; Lolium* species—*L. multiflorum, L. rigidium, L perenne; Digitaria* species—*D. insularis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species *E. colona, E. crus-galli; Eleusine* species—*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Cassia* species, *Sida* species, *Brachiaria* species, *Sporobolus* species—*S. pyramidalis, S. natalensis, S. jacquemontii, S. fertilis, S. africanus S. indicus* and *Solanum* species. Additional weedy plant species found in cultivated areas include Alopecurusmyosuroides, Avenasterilis, Avenasterilisludoviciana, Brachiariaplantaginca, Bromusdiandrus, Bromusrigidus, Cynosurusechinatus, Digitariaciliaris, Digitariaischacmum, Digitariasanguinalis, Echinochloaoryzicola, Echinochloaphyllopogon, Eriochloapunctata, Hordeumglaucum, Hordeumleporinum, Ischaemumrugosum, Leptochloachinensis, Loliumpersicum, *Phalaris minor*, Phalarisparadoxa, Rottboelliaexalta, Setariafaberi, Sctariaviridisvar, robusta-alba schreiber, Setariaviridisvar, robusta-purpurea, Snowdeniapolystachea, Sorghum Sudanese, Alismaplantago-aquatica, Amaranthuslividus, Amaranthusquitensis, Ammaniaauriculata, Ammaniacoccinea, Anthemiscotula, Aperaspica-venti, Bacoparotundifolia, Bidenspilosa, Bidenssubalternans, *Brassica tournefortii, Bromus tectorum*, Camelinamicrocarpa, *Chrysanthemum coronarium*, Cuscutacampestris, Cyperusdijformis, Damasonium minus, Descurainiasophia, Diplotaxistenuifolia, Echiumplantagineum, Elatinetriandravar, pedicellata, *Euphorbia heterophylla, Fallopia convolvulus*, Fimbristylismiliacea, Galcopsistetrahit, Galiumspurium, *Helianthus annuus, Iva xanthifolia, Ixophorusunisetus, Ipomoca indica, Ipomoca purpurea*, Ipomoca sepiaria, Ipomoca aquatic, Ipomoca triloba, Lactucaserriola, Limnocharisflava, Limnophilaerecta, Limnophilasessiliflora, Linderniadubia, Linderniadubiavar, major, Linderniamicrantha, Linderniaprocumbens, Mesembryanthemumcrystallinum, Monochoriakorsakowii, *Monochoria vaginalis, Nesliapaniculata, Papaver rhocas*, Partheniumhysterophorus, Pentziasujfruticosa, *Phalaris minor*, Raphanusraphanistrum, Raphanussativus, Rapistrumrugosum, Rotalaindicavar, uliginosa, Sagittariaguyanensis, Sagittariamontevidensis, Sagittariapygmaca, Salsolaiberica, Scirpusjuncoidesvar, ohwianus, Scirpusmucronatus, Setarialutescens, Sidaspinosa, Sinapisarvensis, Sisymbriumorientale, Sisymbriumthellungii, *Solanum ptycanthum, Sonchus asper*, Sonchusoleraccus, *Sorghum bicolor, Stellaria media*, Thlaspiarvense, *Xanthium strumarium*, Arctotheca calendula, Conyzasumatrensis, Crassocephalumcrepidiodes, Cupheacarthagenenis, Epilobiumadenocaulon, *Erigeron philadelphicus*, Landoltiapunctata, Lepidiumvirginicum, Monochoriakorsakowii, *Solanum americanum, Solanum nigrum, Vulpiabromoides, Youngia japonica*, Hydrillaverticillata, Carduusnutans, Carduuspycnocephalus, Centaureasolstitialis, Cirsiumarvense, Commelinadiffusa, *Convolvulus arvensis*, Daucuscarota, Digitariaischaemum, *Echinochloa crus-pavonis*, Fimbristylismiliacea, Galeopsistetrahit, Galiumspurium, Limnophilaerecta, *Matricaria perforate, Papaver rhoeas, Ranunculus acris*, Solivasessilis, Sphenocleazeylanica, *Stellaria media*, Nassellatrichotoma, Stipaneesiana, *Agrostis stolonifera*, Polygonumaviculare, Alopecurusjaponicus, Beckmanniasyzigachne, *Bromus tectorum, Chloris inflate*, Echinochloaerecta, Portulacaoleracea, and *Senecio vulgaris*.

According to a specific embodiment the weed species is selected from or belong to the group consisting of *Amaranthus: A. palmeri, A. tuberculatus, Lolium rigidum, Ambrosia: A. trifida, A. artemisiifolia, Kochia scoparia, Conyza: C. canadensis, C. bonariensis, Echinochloa, Alopecurus myosuroides, Sorghum halepense, Digitaria insularis, Eleusine indica, Avena fatua, Euphorbia Heterophylla* and *Chenopodium album*.

According to an embodiment, the weed is a parasitic plant. Examples of parasitic plants include, but are not limited to, *Striga* sp, Orobanche sp, Cuscuta sp, Mistletoe.

Different weed may have different growth habits and therefore specific weeds usually characterize a certain crop in given growth conditions.

According to a specific embodiment, the weed is a herbicide resistant weed.

According to a specific embodiment, weed is defined as herbicide resistant when it meets the Weed Science Society of America (WSSA) definition of resistance.

Accordingly, WSSA defines herbicide resistance as "the inherited ability of a plant to survive and reproduce following exposure to a dose of herbicide normally lethal to the wild type. Alternatively, herbicide resistance is defined as "The evolved capacity of a previously herbicide-susceptible weed population to withstand an herbicide and complete its life cycle when the herbicide is used at its normal rate in an agricultural situation" (Source: Heap and Lebaron. 2001 in Herbicide Resistance and World Grains).

As used herein the phrase "weed control" refers to suppressing growth and optionally spread of a population of at least one weed species of interest and even reducing the size of the population in a given growth area.

According to a specific embodiment, the growth area is an urban area, e.g., golf courses, athletic fields, parks, cemeteries, roadsides, home gardens/lawns and the like.

According to an additional or alternative embodiment, the growth area is a rural area.

According to an additional or an alternative embodiment, the growth area is an agricultural growth area e.g., open field, greenhouse, plantation, vineyard, orchard and the like.

As mentioned, weed control according to the present teachings is effected by reducing fitness of the at least one weed species of interest.

As used herein "fitness" refers to the relative ability of the weed species of interest to develop, reproduce or propagate and transmit its genes to the next generation. As used herein "relative" means in comparison to a weed of the same species not having been artificially pollinated with the pollen of the invention and grown under the same conditions.

It will be appreciated that the effect of pollen treatment according to the present teachings is typically manifested in the first generation after fertilization.

The fitness may be affected by reduction in productiveness, propagation, fertility, fecundity, biomass, biotic stress tolerance, abiotic stress tolerance and/or herbicide resistance.

As used herein "productivity" refers to the potential rate of incorporation or generation of energy or organic matter by an individual, population or trophic unit per unit time per unit area or volume; rate of carbon fixation.

As used herein "fecundity" refers to the potential reproductive capacity of an organism or population, measured by the number of gametes.

According to a specific embodiment, the pollen affects any stage of seed development or germination.

According to a specific embodiment, the reduction in productiveness is manifested by at least one of:
  (i) inability to develop an embryo;
  (ii) embryo abortion;
  (iii) seed non-viability;
  (iv) seed that cannot fully develop;
  (v) seed that is unable to germinate; and/or
  (vi) seed set number.

It will be appreciated that when pollen reduces the productiveness, fertility, propagation ability or fecundity of the weed in the next generation it may be referred to by the skilled artisan as sterile pollen, though it fertilizes the weed of interest. Hence, sterile pollen as used herein is still able to fertilize.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization, second generation after fertilization or third generation after fertilization.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization.

According to a specific embodiment, reduced fitness results from reduction in tolerance to biotic or abiotic conditions e.g., herbicide resistance.

Non-limiting examples of abiotic stress conditions include, salinity, osmotic stress, drought, water deprivation, excess of water (e.g., flood, waterlogging), etiolation, low temperature (e.g., cold stress), high temperature, heavy metal toxicity, anaerobiosis, nutrient deficiency (e.g., nitrogen deficiency or nitrogen limitation), nutrient excess, atmospheric pollution, herbicide, pesticide and UV irradiation.

Biotic stress is stress that occurs as a result of damage done to plants by other living organisms, such as bacteria, viruses, fungi, parasites, beneficial and harmful insects, weeds, and cultivated or native plants.

Examples of herbicides which are contemplated according to the present teachings, include, but are not limited to, ACCase inhibitors, ALS inhibitors, Photosystem II inhibitors, PSII inhibitor (Ureas and amides), PSII inhibitors (Nitriles), PSI Electron Diverter, PPO inhibitors, Carotenoid biosynthesis inhibitors, HPPD inhibitors, Carotenoid biosynthesis (unknown target), EPSP synthase inhibitors, Glutamine synthase inhibitors, DHP synthase inhibitors, Microtubule inhibitors, Mitosis inhibitors, Long chain fatty acid inhibitors, Cellulose inhibitors, Uncouplers, Lipid Inhibitors (thiocarbamates), Synthetic Auxins, Auxin transport inhibitors, Cell elongation inhibitors, Antimicrotubule mitotic disrupter, Nucleic acid inhibitors or any other form of herbicide site of action.

As used herein "pollen" refers to pollen that is able to fertilize the weed species of interest and therefore competes with native pollination.

Alternatively, when native pollen competition does not exist, or very low levels of native pollen are present, pollination by the designed pollen inhibits apomixis of weeds and by this reduces their quantities as well [Ribeiro et al. 2012].

According to a specific embodiment, the pollen is of the same species as of the target weed (e.g., invasive, aggressive weed).

According to a specific embodiment, the pollen exhibits susceptibility to a single growth condition e.g., herbicide, temperature.

According to a specific embodiment, the pollen exhibits susceptibility to multiple growth conditions e.g., different herbicides (see Example 9).

According to a specific embodiment, the pollen is non-genetically modified.

The pollen may therefore be of a naturally occurring plant that reduces the fitness of the at least one weed species of interest. According to a specific embodiment, *A. palmeri* or *A. tuberculatus* susceptible seeds are available from the Agriculture Research Service National Plant Germplasm System plant introduction (USDA-ARS_NPGS PI) as well as from various locations in Israel.

Alternatively or additionally, the pollen may be of a plant that has been selected towards producing pollen that reduces the fitness of the at least one weed species of interest.

Selection can be effected by way of exposing the weed to various concentrations of, for example, a herbicide or a plurality of different herbicides, and selecting individuals which show increased susceptibility to the herbicide or different herbicides (see Example 9, which is incorporated herein). Alternatively or additionally, different plants exhibiting susceptibility to different herbicides can be crossed to generate a plant exhibiting susceptibility to a number of herbicides of interest.

It will be appreciated that such breeding need not engage into pedigree breeding programs as the mere product is the pollen of a weedy plant.

According to a specific embodiment, there is provided a method of producing pollen that reduces fitness of at least one weed species of interest, the method comprising treating the weed species of interest (e.g., seeds, seedlings, tissue/cells) or pollen thereof with an agent that reduces fitness.

When needed (such as when treating that weed (e.g., seeds, seedlings, tissue/cells) the method further comprises growing or regenerating the plant so as to produce pollen.

According to a specific embodiment, the method comprises harvesting pollen from the weed species of interest following treating with the agent that reduces the fitness.

It will be appreciated that the pollen may be first harvested and then treated with the agent (e.g., radiation) that reduces the fitness of the weed species of interest.

Alternatively or additionally, the pollen is produced from a plant having an imbalanced chromosome number (genetic load) with the weed species of interest.

Thus, for example, when the weed of interest is diploid, the plant producing the pollen is treated with an agent rendering it polyploid, typically tetraploids are selected, such that upon fertilization with the diploid female plant an aborted or developmentally arrested, not viable seed set are created. Alternatively, a genomically imbalanced plant is produced which rarely produces a seed set.

A specific description of such a treatment is provided in Examples 18 and 27 of the Examples section which follows and should be considered as part of the specification.

According to a specific embodiment, the weed (or a regenerating part thereof) is subjected to a polyploidization protocol using a polyploidy inducing agent, that produces plants which are able to cross but result in reduced productiveness, Thus, according to some embodiments of the invention, the polyploid weed has a higher chromosome number than the wild type weed species (e.g., at least one chromosome set or portions thereof) such as for example two folds greater amount of genetic material (i.e., chromosomes) as compared to the wild type weed. Induction of polyploidy is typically performed by subjecting a weed tissue (e.g., seed) to a G2/M cycle inhibitor.

Typically, the G2/M cycle inhibitor comprises a microtubule polymerization inhibitor.

Examples of microtubule cycle inhibitors include, but are not limited to oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophosmethyl, taxol, vinblastine, griseofulvin, caffeine, bis-ANS, maytansine, vinbalstine, vinblastine sulphate and podophyllotoxin.

According to a specific embodiment, the microtubule cycle inhibitor is colchicine.

Still alternatively or additionally, the weed may be selected producing pollen that reduces fitness of the weed species of interest by way of subjecting it to a mutagenizing agent and if needed further steps of breeding.

Thus, weed can be exposed to a mutagen or stress followed by selection for the desired phenotype (e.g., pollen sterility, herbicide susceptibility).

Examples of stress conditions which can be used according to some embodiments of the invention include, but are not limited to, X-ray radiation, gamma radiation, UV radiation or alkylating agents such as NEU, EMS, NMU and the like. The skilled artisan will know which agent to select.

According to a specific embodiment, the stress is selected from the group consisting of X-ray radiation, gamma radiation, UV radiation. For example. pollen of the weed can be treated with the agent that reduces the fitness (e.g., radiation) following harvest.

A specific description of such treatments are provided in Examples 19, 24, 25 and 26 of the Examples section which follows and should be considered as part of the specification.

Guidelines for plant mutagenesis are provided in K Lindsey Plant Tissue Culture Manual-Supplement 7: Fundamentals and Applications, 1991, which is hereby incorporated in its entirety.

Other mutagenizing agents include, but are not limited to, alpha radiation, beta radiation, neutron rays, heating, nucleases, free radicals such as but not limited to hydrogen peroxide, cross linking agents, alkylating agents, BOAA, DES, DMS, EI, ENH, MNH, NMH Nitrous acid, bisulfate, base analogs, hydroxyl amine, 2-Naphthylamine or alfatoxins.

Alternatively or additionally, the pollen may be genetically modified pollen (e.g., transgenic pollen, DNA-editing).

Numerous methods are known for exploiting genetic modification to render it suitable for reducing the fitness of a weed species of interest.

Thus, according to a specific embodiment, the pollen is genetically modified pollen.

According to other specific embodiments, the trait being inherited upon artificial pollination with the pollen of the invention is selected from the group consisting of embryo abortion, seed non-viability, seeds with structural defects, seeds that are unable to germinate, abiotic/biotic stress susceptibility (e.g., herbicide susceptibility) or induced death or sensitivity upon chemical or physical induction or any other inherited property that will enable controlled reduction of weed population size.

Often sterile pollen results in a seedless plant. A plant is considered seedless if it is not able to produce seeds, traces of aborted seeds or a much-reduced number of seeds. In other cases the pollen will produce plants with seeds that are unable to germinate or develop e.g., no embryo or embryo abortion.

According to a specific embodiment, the pollen is genetically modified to express an exogenous transgene that upon fertilization will reduce fitness of the weed of interest (next generation). Such a gene is termed a "disrupter gene". According to some embodiments, the disrupter gene causes kills the weed species of interest, accordingly it is termed a "death gene".

According to a specific embodiment, the pollen is genetically modified to express a silencing agent that upon fertilization will reduce fitness of the weed of interest (next generation).

According to a specific embodiment, the pollen is genetically modified to express a genome editing agent that upon fertilization will reduce fitness of the weed of interest (next generation).

In some embodiments of the invention, the genetic modification is effected in an inducible manner to minimize the effect on the weed producing the pollen product of the invention (i.e., that reduces the fitness of the plant of interest).

Following are methods which can be used to induce pollen sterility. Further details of these methods are provided in Examples 10-11, 13-18 and 20, each of which is incorporated into this section in its entirety.

Genetic Use Restriction Technology (GURT).

Embodiments of the invention make use of this technology which provides specific genetic switch mechanisms that hamper reproduction (variety specific V-GURT) or the expression of a trait (trait-specific T-GURT) in a genetically modified (transgenic) plant.

Variety GURT (also known as suicide/sterile seed/gene technology or terminator technology) is designed to control plant fertility or seed development through a genetic process triggered by a chemical inducer that will allow the plant to grow and to form seeds, but will cause the embryo of each of those seeds to produce a cell toxin that will prevent its germination if replanted, thus causing second generation seeds that will not germinate.

T-GURT (ironically known as traitor technology) is designed to switch on or off a trait (such as herbicide/cold/drought/stress tolerance, pest resistance, germination, flowering or defense mechanisms) using inducible promoters regulating the expression of the transgene through induced gene silencing (e.g., by antisense suppression) or by excision of the transgene using a recombinase. In this case, the genetic modification is activated by a chemical treatment or by physical factors e.g., environmental factors such as heat.

These methods are reviewed by Lombardo 2014 Plant Biotechnology Journal 12:995-1005, U.S. Pat. No. 5,364,780, WO9403619, WO9404393, U.S. Pat. No. 5,723,765 each of which is incorporated herein by reference.

Both methods can rely on site-specific recombination of DNA in plant cells. Typically the recombination system employed is from bacteriophage P1. The system comprises a recombinase (Cre) and recombination sites (loxP). In the presence of Cre, recombination between loc sites occurs on supercoiled, nicked, circular or linear DNA. Alternative recombination systems are: Flp/frt, R/RS, Gin/Gix. Specific signal sequences can be selected from the group comprising LOX sequences and sequences recognizable by either flippase, resolvase, FLP, SSV1-encoded integrase, or transposase and the second gene that encodes a specific recombinase can be selected from the group comprising CRE, flippase, resolvase, FLP, SSV1-encoded integrase, and transposase.

The activation of a cytotoxic gene using this system is a well known way of producing sterile plants.

For V-GURTs, essentially three different restriction mechanisms are proposed (Visser et al., 2001 Biotechnol. Dev. Monit. 48, 9-12). The first mechanism of action is that described in the patent (U.S. Pat. No. 5,723,765) by the USDA and Delta & Pine Land (nominally the first V-GURT). This GURT is based on the transfer of a combination of three genes (transgenes), two derived from bacteria and one from another plant, into a plant's cells:

1. A gene coding for a cytotoxic protein (the terminator or lethal gene) e.g., under control of a late embryogenesis abundant (LEA) promoter linked to a DNA spacer (blocking) sequence flanked by specific excision sites (lox sequence) that prevents the activation of the terminator gene. In the '765 patent, the cytotoxic protein is the ribosome inactivating protein (RIP), otherwise known as saporin derived from *Saponaria officinalis*, which prevents plant cells from synthesizing proteins. Barnase is an alternative for RIP, as will be further described hereinbelow;

2. A site-specific recombinase gene under the control of a constitutively active promoter (e.g., CaMV 35S) containing one or more tet operons that is subject to repression by the Tet repressor. This gene encodes a recombinase (e.g., Cre) that cuts the specific excision sites flanking the blocking sequence linked to the toxic gene;

3. A repressor gene (e.g., Tn10 tet) under the control of a constitutive promoter and encoding a protein that binds to the responsive operon (e.g., tet), preventing the expression of the recombinase gene. The presence of an external stimulus (chemical or physical inducer) prevents binding of the repressor to the operon. The external stimulus can be chemical inducers such as agrochemicals and antibiotics or physical such as temperature.

In another embodiment of the method, which is also contemplated herein, the recombinase gene is directly linked to an inducible promoter (U.S. Pat. No. 5,723,765).

Potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide [Reviewed in Padidam et al., 2003].

It will be appreciated that in sharp contrast to prior art methods, the genetically modified pollen is that of the weed and not that of the crop.

U.S. Pat. No. 5,925,808 describes embodiments of the Genetic Use Restriction Technology, and is hereby incorporated by reference in its entirety.

Following is a non-limiting example, for the use of GURT in conferring weeds with reduced fitness.

Thus, the following constructs can be produced.

1. A gene which expression results in an altered plant phenotype e.g., disrupter gene, linked to a transiently active promoter, the gene and promoter being separated by a blocking sequence flanked on either side by specific excision sequences.

2. A second gene that encodes a recombinase specific for the specific excision sequences linked to a repressible promoter.

3. A third gene that encodes the repressor specific for the repressible promoter.

Plasmid sequences and procedures can be used as described in U.S. Pat. No. 5,925,808, supra:

According to an exemplary embodiment, the death gene used is RIP (ribosomal inhibitor protein, sequence of a complete RIP gene, saporin 6: GenBank ID SOSAP6, Accession No. X15655) or barnase (Genbank Accession M14442). The CRE Gene is under the control of a Tetracycline-derepressible 35S Promoter. The third plasmid comprises a Tet Repressor Gene Driven by a 35S Promoter.

The transiently active promoter in the first plasmid is expressed during embryogenesis, seed development or seed germination. Optional gene promoters include promoters of embryogenesis genes such as late embryogenesis abundant genes LEA1, LEA2, LEA3, LEA4, LEA5, DEHYDRIN and SMP (Pedrosa et al., 2015), promoters of seed development genes such as LEAFY COTYLEDON genes, including, but not limited to, LEC1, LEC2 and FUSCA3 (FUS3), or ABSCISIC ACID INSENSITIVE 3 (ABI3) (Santos-Mendoza et al., 2008). Additional promoters of seed development genes can be taken from multiple comprehensive studies that identified a long list of related genes (see Le et al., 2010 and McElver J et al., 2001). Promoters of Germination genes include but are not limited to Expansin (Chen and Bradford., 2000), endo-β-mannase (Nonogaki H et al., 2000), β-1,3-glucanase (Leubner-Metzger and Meins, 2000 and Wu et al., 2001), extension like protein ERP1 (Dubreucq et al., 2000) as well as genes that are related to abscisic acid (ABA) and gibberellic acid (GA) biosynthesis (Shu et al., 2015 and Toorop et al., 2000).

Other construct systems which can be used rely on a transcriptional inducible system. In such constructs, transcription is reversibly turned on or off in the presence of an analyte e.g., antibiotic e.g., tetracycline or one of its derivatives (e.g. doxycycline). Such are described in Wikipedia and is summarized infra. Briefly, the Tet-Off system makes use of the tetracycline transactivator (tTA) protein, which is created by fusing one protein, TetR (tetracycline repressor), found in *Escherichia coli* bacteria, with the activation domain of another protein, VP16, found in the Herpes Simplex Virus.

The resulting tTA protein is able to bind to DNA at specific TetO operator sequences. In most Tet-Off systems, several repeats of such TetO sequences are positioned upstream of a minimal promoter. The entirety of several TetO sequences with a minimal promoter is called a tetracycline response element (TRE), because it responds to binding of the tetracycline transactivator protein (tTA) by increased expression of the gene or genes downstream of its promoter. In a Tet-Off system, expression of TRE-controlled genes can be repressed by tetracycline and its derivatives (e.g., doxycycline, anhydrotetracycline). They bind tTA and render it incapable of binding to TRE sequences, thereby preventing transactivation of TRE-controlled genes. A Tet-On system works similarly, but in the opposite fashion. While in a Tet-Off system, tTA is capable of binding the operator only if not bound to tetracycline or one of its derivatives, such as doxycycline, in a Tet-On system, the reverse tetracycline transactivator (rtTA) protein is capable of binding the operator only if bound by a tetracycline. Thus, the introduction of doxycycline to the system initiates the transcription of the genetic product.

Examples for use of these systems include but not limited to the following set of constructs that relies on the Tet ON system:

1. A gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to an operator that is upstream to the promoter and is responsive to an activator.

3. A third gene that encodes the activator specific for the operator in the second plasmid under a constitutive promoter.

Applied inducer binds the activator protein eliciting a conformational change to its active form.

According to an exemplary embodiment, the death gene used under the control of an embryogenesis, seed development or seed germination promoter is RIP (ribosomal inhibitor protein, sequence of a complete RIP gene, saporin 6: GenBank ID SOSAP6, Accession No. X15655) or barnase (Genbank Accession M14442). The CRE Gene is under the control of a Tet-ON TRE and the third plasmid is a constitutive promoter upstream of an rtTA. Upon application of tetracycline or its derivatives such as doxycycline the rtTA becomes activated and results in expression of the CRE recombinase and consequently activates the death gene.

Another optional set of plasmids that can be used is a simplified two plasmids system that again relies on the Tet-ON system:

1. A gene which expression results in an altered plant phenotype linked to a transiently active promoter and an operator that is upstream to the promoter and is responsive to an activator.

2. A second gene that encodes the activator specific for the operator from the first plasmid under a constitutive promoter.

According to an exemplary embodiment, the death gene used is RIP (ribosomal inhibitor protein, sequence of a complete RIP gene, saporin 6: GenBank ID SOSAP6, Accession No. X15655) or barnase (Genbank Accession M14442). The death gene is under the dual control of both a promoter that is active during embryogenesis, seed development or seed germination as well as a Tet-ON TRE.

And the second plasmid is a constitutive promoter upstream of an rtTA. Upon application of tetracycline or its derivatives such as doxycycline the rtTA becomes activated and results in activation of the death gene.

Yet alternatively or additionally, plants which produce pollen capable of reducing fitness of a weed species of interest can be generated by a hybrid GURT method whereby a dual complementary male and female plant genetic recombination systems are used (see Examples 13-14, which are hereby incorporated into this section of the specification in its entirety).

A weed sterile line is being produced by crossing between two homozygous transformed plants. The male and female plants are each transformed with a plasmid encoding a disrupter gene controlled by a transiently active promoter, the gene and promoter being separated by a blocking sequence flanked on either side by specific excision sequences (such as lox or frt excision sequences). In addition the plasmid contains a second gene that encodes a genetic recombination enzyme (such as cre recombinase or flp flippase) specific for the excision sequences in the opposite sex (namely, the recombination enzyme of the female plant cut the excision sequence in the male and vice versa). These recombination enzymes are under the control of a promoter that is active post seed germination stage. The transformed plasmid both in the male and in the female homozygous lines are inserted to the same genomic locus position.

The following plasmid is transformed into the female plant:

Plasmid encoding a barnase or RIP gene under the control of a specific embryogenesis, seed development or germination promoter whereas the gene and promoter being separated by a blocking sequence flanked on either side by specific excision lox sequences and a second gene encoding for a flippase recombination enzyme under a promoter that is active post seed germination.

The following plasmid is transformed into the male plant:

Plasmid encoding a barnase or RIP gene under the control of a specific embryogenesis, seed development or germination promoter whereas the gene and promoter are being separated by a blocking sequence flanked on either side by specific excision frt sequences and a second gene encoding for a cre recombinase recombination enzyme under a promoter that is active post seed germination.

Lines are being selected such that both insertions to both male and female are on the exact same genomic position.

Only upon crossing between these male plants with these female plants both recombination events by flp and cre are occurring thus yielding pollen that have a barnase or RIP gene under the control of a specific embryogenesis, seed development or germination promoter.

Another embodiment of V-GURT contemplated herein (see U.S. Pat. No. 5,808,034, herein incorporated in its entirety) is based on a reversed process because it is characterized by the presence of a gene encoding a disrupter protein that is active in embryogensis seed development or seed germination thus resulting in loss of productiveness. Only upon exposure to a chemical or physical inducer that result in inhibition of the disrupter gene the plant is capable of reproducing normally. It will be appreciated that in sharp contrast to prior art methods, the genetically modified pollen contains the disrupter gene under the regulation of a transiently active promoter that is expressed during embryogenesis, seed development or seed germination and not male flower specific promoters.

Thus, a sterile line can be produced using two plasmids:

1. Plasmid encoding for a disrupter protein under a promoter that is active in the embryo or seed, which makes it sterile where the gene promoter is under the control of a specific operator sequence responsive to repression by a repressor protein.

2. A repressor protein, whose gene is under the control of a constitutive promoter. When binding to a specific chemical the repressor can bind the operator from the first plasmid and inhibit the expression of the disrupter protein. According to an exemplary embodiment, the disrupter gene used under the control of an embryogenesis, seed development or seed germination promoter as well as the control of at least one TetO element is RIP (ribosomal inhibitor protein, sequence of a complete RIP gene, saporin 6: GenBank ID SOSAP6, Accession No. X15655) or barnase (Genbank Accession M14442). The reverse TetR gene (mutated form of the original TetR) is under a constitutive promoter. Upon application of tetracycline or its derivatives such as doxycycline the reverse TetR becomes activated and results in inhibition of expression of the disrupter induced gene.

Alternatively, it can be produced by using the Tet-Off system with the following two plasmids:

1. Plasmid encoding for a disrupter protein under a promoter that is active in the embryo or seed, which makes the plant sterile where the gene promoter is under the control of a specific operator sequence responsive to activation by an activator protein.

2. An activator protein, whose gene is under the control of a constitutive promoter. Upon specific chemical binding to this activator it becomes non-active and can no longer activate the transcription of the first plasmid.

According to an exemplary embodiment, the disrupter gene used under the control of an upstream TRE followed by an embryogenesis, seed development or seed germination promoter is RIP (ribosomal inhibitor protein, sequence of a complete RIP gene, saporin 6: GenBank ID SOSAP6, Accession No. X15655) or barnase (Genbank Accession M14442). The tTA Gene is under a constitutive promoter. Upon application of tetracycline or its derivatives such as doxycycline the tTA becomes inactivated and results in inhibition of expression of the disrupter induced gene.

It will be appreciated that in the reverse process the disrupter gene is active however upon application of an inducer, the disrupter gene is turned off allowing the plant to survive and reproduce.

Thus, as mentioned, the disrupter gene promoter is under the control of a specific operator sequence. A further repressor protein, which gene is under control of a chemically or physically inducible promoter, can bind to the operator, inhibiting the expression of the disrupter protein. In the absence of the exogenous chemical inducer, no repressor protein is expressed; therefore, the breeder must apply the specific chemical inducer throughout the process of seed multiplication to inactivate the disrupter gene that causes sterility, terminating the application only at the time of selling the seeds.

A further technology contemplated herein refers to the recoverable block of function (RBF), which consists of a blocking sequence (e.g., encoding a barnase) linked to the gene of interest and a recovery sequence (e.g., encoding a barstar), expressed under control of sulfhydryl endopeptidase (SH-EP) and heat shock (HS) promoters, respectively, and all contained in a single insert. The natural expression of the barnase in embryos and sprouts confers cell death or prevents sexual reproduction (by blocking mRNA synthesis and germination) in the natural environment. The expression of the recovery sequence is induced by an artificial external stimulus such as a heat shock treatment or chemical application; recovery of the blocked function results in the 'restoration' of the viable/fertile phenotype. Any seed formed from hybridization between wild weed and the GM pollen that contain the RBF will be unable to germinate because of the action of the blocking sequence. It will be appreciated that in sharp contrast to prior art methods, the genetically modified pollen with the RBF system that is used in the artificial pollination and is aimed at weed control does not have a gene of interest coupled to it. Alternatively, or additionally the plant can be transformed with any gene that results in reduced fitness (destruction gene) which expression can be induced (see Example 10-14, 21-22 for specific embodiments.

Various inducible systems are known in the art. These include, but are not limited to, AlcR based ethanol inducible system, Tetracycline system, steroid-inducible systems such as but not limited to Glucocorticoid receptor-based, Dexamethasone-inducible, Estradiol inducible or Estrogen receptor-based, insecticide inducible systems such as but not limited to Ecdysone receptor-based, or ACEI-based, copper-inducible system. Additional inducible systems are Benzo-thiadiazole-inducible and Safener-inducible, Tebufenozide inducible or, Methoxyfenozide inducible systems [Padidam et al., 2003].

In the same manner the following constructs can be prepared, provided they are under an inducible regulation. Thus, transgenic weeds expressing EtoH inducible death gene are being produced using insertion of a plasmid encoding for AlcR based EtoH inducible promoter linked to a barnase gene or a RIP gene as explained in Example 21 or transgenic plants expressing EtOH inducible EPSPS anti sense RNA to reduce EPSPS levels upon ethanol application as explained in Example 22.

Examples of genes that can be modulated in order to reduce tolerance to biotic or abiotic stress include, but are not limited to, HSF, MYB, MYC, AP2/ERF, NAC, ZF, HSP, MAPK, LEA, SOS or CYP (Atkinson N J and Urwin P E, 2012); or microRNA families such as MIR156, MIR166, MIR167, MIR 169 (Khraiwesh, B. et al., 2012).

Another option is generating a weed strain that produces pollen that is genetically modified to express an inhibitor of a gene that is responsible for herbicide resistance or tolerance (e.g., biotic or abiotic) such as a silencing agent or DNA editing agent (e.g., CRISPR-Cas9, as further detailed below) that modulates expression of a target molecule e.g., herbicide targeted molecule such as but not limited to genes related to ACCase, ALS, Photosystem II, PSI Electron Diverter, PPO, Carotenoid biosynthesis, HPPD, EPSP synthase, Glutamine synthase, DHP synthase, Mitosis, Auxin transport, Uncouplers, Antimicrotubule mitotic disrupter, Cell elongation or in the process of generation of Microtubule, Long chain fatty acid, Cellulose, Lipid, Nucleic acid or modulating expression of any other critical gene participating in the fertilization process, embryonic development, seed development or germination process.

Examples of platform technologies that can be used to down-regulate gene expression include, but are not limited to downregulation (gene silencing) of the transcription or translation product of an endogenous gene can be achieved by co-suppression, antisense suppression, RNA intereference and ribozyme molecules.

Co-suppression (sense suppression)—Inhibition of the endogenous gene can be achieved by co-suppression, using an RNA molecule (or an expression vector encoding same) which is in the sense orientation with respect to the transcription direction of the endogenous gene. The polynucleotide used for co-suppression may correspond to all or part of the sequence encoding the endogenous polypeptide and/ or to all or part of the 5' and/or 3' untranslated region of the endogenous transcript; it may also be an unpolyadenylated RNA; an RNA which lacks a 5' cap structure; or an RNA which contains an unsplicable intron.

In some embodiments, the polynucleotide used for co-suppression is designed to eliminate the start codon of the endogenous polynucleotide so that no protein product will be translated. Methods of co-suppression using a full-length cDNA sequence as well as a partial cDNA sequence are known in the art (see, for example, U.S. Pat. No. 5,231,020).

According to some embodiments of the invention, down-regulation of the endogenous gene is performed using an amplicon expression vector which comprises a plant virus-derived sequence that contains all or part of the target gene but generally not all of the genes of the native virus. The viral sequences present in the transcription product of the expression vector allow the transcription product to direct its own replication. The transcripts produced by the amplicon may be either sense or antisense relative to the target sequence [see for example, Angell and Baulcombe, (1997) *EMBO J.* 16:3675-3684; Angell and Baulcombe, (1999) *Plant J.* 20:357-362, and U.S. Pat. No. 6,646,805, each of which is herein incorporated by reference].

Antisense suppression-Antisense suppression can be performed using an antisense polynucleotide or an expression vector which is designed to express an RNA molecule complementary to all or part of the messenger RNA (mRNA) encoding the endogenous polypeptide and/or to all or part of the 5' and/or 3' untranslated region of the endogenous gene. Over expression of the antisense RNA molecule can result in reduced expression of the native (endogenous) gene. The antisense polynucleotide may be fully complementary to the target sequence (i.e., 100% identical to the complement of the target sequence) or partially complementary to the target sequence (i.e., less than 100% identical, e.g., less than 90%, less than 80% identical to the complement of the target sequence).

Antisense suppression may be used to inhibit the expression of multiple proteins in the same plant (see e.g., U.S. Pat. No. 5,942,657). In addition, portions of the antisense nucleotides may be used to disrupt the expression of the target gene. Generally, sequences of at least about 50 nucleotides, at least about 100 nucleotides, at least about 200 nucleotides, at least about 300, at least about 400, at least about 450, at least about 500, at least about 550, or greater may be used. Methods of using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference.

Efficiency of antisense suppression may be increased by including a poly-dT region in the expression cassette at a position 3' to the antisense sequence and 5' of the polyadenylation signal [See, U.S. Patent Publication No. 20020048814, herein incorporated by reference].

RNA intereference-RNA intereference can be achieved using a polynucleotide, which can anneal to itself and form a double stranded RNA having a stem-loop structure (also called hairpin structure), or using two polynucleotides, which form a double stranded RNA.

For hairpin RNA (hpRNA) interference, the expression vector is designed to express an RNA molecule that hybridizes to itself to form a hairpin structure that comprises a single-stranded loop region and a base-paired stem.

In some embodiments of the invention, the base-paired stem region of the hpRNA molecule determines the specificity of the RNA interference. In this configuration, the sense sequence of the base-paired stem region may correspond to all or part of the endogenous mRNA to be down-regulated, or to a portion of a promoter sequence controlling expression of the endogenous gene to be inhibited; and the antisense sequence of the base-paired stem region is fully or partially complementary to the sense sequence. Such hpRNA molecules are highly efficient at inhibiting the expression of endogenous genes, in a manner which is inherited by subsequent generations of plants [See, e.g., Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genct. 4:29-38; Chuang and Meyerowitz, (2000) Proc. Natl. Acad. Sci. USA 97:4985-4990; Pandolfini et al., BMC Biotechnology 3:7; Panstruga, et al., (2003) Mol. Biol. Rep. 30:135-140; and U.S. Patent Publication No. 2003/0175965; each of which is incorporated by reference].

According to some embodiments of the invention, the sense sequence of the base-paired stem is from about 10 nucleotides to about 2,500 nucleotides in length, e.g., from about 10 nucleotides to about 500 nucleotides, e.g., from about 15 nucleotides to about 300 nucleotides, e.g., from about 20 nucleotides to about 100 nucleotides, e.g., or from about 25 nucleotides to about 100 nucleotides.

According to some embodiments of the invention, the antisense sequence of the base-paired stem may have a length that is shorter, the same as, or longer than the length of the corresponding sense sequence.

According to some embodiments of the invention, the loop portion of the hpRNA can be from about 10 nucleotides to about 500 nucleotides in length, for example from about 15 nucleotides to about 100 nucleotides, from about 20 nucleotides to about 300 nucleotides or from about 25 nucleotides to about 400 nucleotides in length.

According to some embodiments of the invention, the loop portion of the hpRNA can include an intron (ihpRNA), which is capable of being spliced in the host cell. The use of an intron minimizes the size of the loop in the hairpin RNA molecule following splicing and thus increases efficiency of the interference [See, for example, Smith, et al., (2000) Nature 407:319-320; Wesley, et al., (2001) Plant J. 27:581-590; Wang and Waterhouse, (2001) Curr. Opin. Plant Biol. 5:146-150; Helliwell and Waterhouse, (2003) Methods 30:289-295; Brummell, et al. (2003) Plant J. 33:793-800; and U.S. Patent Publication No. 2003/0180945; WO 98/53083; WO 99/32619; WO 98/36083; WO 99/53050; US20040214330; US20030180945; U.S. Pat. Nos. 5,034, 323; 6,452,067; 6,777,588; 6,573,099 and 6,326,527; each of which is herein incorporated by reference].

In some embodiments of the invention, the loop region of the hairpin RNA determines the specificity of the RNA interference to its target endogenous RNA. In this configuration, the loop sequence corresponds to all or part of the endogenous messenger RNA of the target gene. See, for example, WO 02/00904; Mette, et al., (2000) EMBO J 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99 (4): 16499-16506; Sijen, et al., Curr. Biol. (2001) 11:436-440), each of which is incorporated herein by reference.

For double-stranded RNA (dsRNA) interference, the sense and antisense RNA molecules can be expressed in the same cell from a single expression vector (which comprises sequences of both strands) or from two expression vectors (each comprising the sequence of one of the strands). Methods for using dsRNA interference to inhibit the expression of endogenous plant genes are described in Waterhouse, et al., (1998) Proc. Natl. Acad. Sci. USA 95:13959-13964; and WO 99/49029, WO 99/53050, WO 99/61631, and WO 00/49035; each of which is herein incorporated by reference.

According to some embodiments of the invention, RNA intereference is effected using an expression vector designed to express an RNA molecule that is modeled on an endogenous micro RNAs (miRNA) gene. Micro RNAs (miRNAs) are regulatory agents consisting of about 22 ribonucleotides and highly efficient at inhibiting the expression of endogenous genes [Javier, et al., (2003) Nature 425:257-263]. The miRNA gene encodes an RNA that forms a hairpin structure containing a 22-nucleotide sequence that is complementary to the endogenous target gene.

Ribozyme-Catalytic RNA molecules, ribozymes, are designed to cleave particular mRNA transcripts, thus preventing expression of their encoded polypeptides. Ribozymes cleave mRNA at site-specific recognition sequences. For example, "hammerhead ribozymes" (see, for example, U.S. Pat. No. 5,254,678) cleave mRNAs at locations dictated by flanking regions that form complementary base pairs with the target mRNA. The sole requirement is that the target RNA contains a 5'-UG-3' nucleotide sequence. Hammerhead ribozyme sequences can be embedded in a stable RNA such as a transfer RNA (tRNA) to increase cleavage efficiency in vivo [Perriman et al. (1995) Proc. Natl. Acad. Sci. USA, 92 (13): 6175-6179; de Feyter and Gaudron Methods in Molecular Biology, Vol. 74, Chapter 43, "Expressing Ribozymes in Plants", Edited by Turner, P. C, Humana Press Inc., Totowa, N.J.; U.S. Pat. No. 6,423, 885]. RNA endoribonucleases such as that found in Tetrahymena thermophila are also useful ribozymes (U.S. Pat. No. 4,987,071).

Constructs useful in the methods according to some embodiments of the invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein said nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of promoters useful for the methods of some embodiments of the invention are presented in Table 1.

TABLE 1

Exemplary constitutive promoters for use in the performance of some embodiments of the invention

| Gene Source | Expression Pattern | Reference |
|---|---|---|
| Actin | constitutive | McElroy etal, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |

According to some embodiments of the invention, over-expression is achieved by means of genome editing. However, the same means can be used to down-regulate gene expression all dependent on the design of the gene editing tool.

Genome editing is a reverse genetics method which uses artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location.

To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Over expression of a polypeptide by genome editing can be achieved by: (i) replacing an endogenous sequence encoding the polypeptide of interest, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-UTR and/or 3'-UTR). Downregulation of a gene of interest can be achieved by introducing point mutations which result in down-regulation of the gene encoding the polypeptide of interest (e.g., by altering the regulatory sequences such as promoter, enhancers, 5'-UTR and/or 3'-UTR, inserting mutations in a catalytic site or protein-protein interaction interface).

Homology Directed Repair (HDR).

Homology Directed Repair (HDR) can be used to generate specific nucleotide changes (also known as gene "edits") ranging from a single nucleotide change to large insertions. In order to utilize HDR for gene editing, a DNA "repair template" containing the desired sequence must be delivered into the cell type of interest with the guide RNA [gRNA(s)] and Cas9 or Cas9 nickase. The repair template must contain the desired edit as well as additional homologous sequence immediately upstream and downstream of the target (termed left and right homology arms). The length and binding position of each homology arm is dependent on the size of the change being introduced. The repair template can be a single stranded oligonucleotide, double-stranded oligonucleotide, or double-stranded DNA plasmid depending on the specific application. It is worth noting that the repair template must lack the Protospacer Adjacent Motif (PAM) sequence that is present in the genomic DNA, otherwise the repair template becomes a suitable target for Cas9 cleavage. For example, the PAM could be mutated such that it is no longer present, but the coding region of the gene is not affected (i.e. a silent mutation).

The efficiency of HDR is generally low (<10% of modified alleles) even in cells that express Cas9, gRNA and an exogenous repair template. For this reason, many laboratories are attempting to artificially enhance HDR by synchronizing the cells within the cell cycle stage when HDR is most active, or by chemically or genetically inhibiting genes involved in Non-Homologous End Joining (NHEJ). The low efficiency of HDR has several important practical implications. First, since the efficiency of Cas9 cleavage is relatively high and the efficiency of HDR is relatively low, a portion of the Cas9-induced double strand breaks (DSBs) will be repaired via NHEJ. In other words, the resulting population of cells will contain some combination of wild-type alleles, NHEJ-repaired alleles, and/or the desired HDR-edited allele.

Therefore, it is important to confirm the presence of the desired edit experimentally, and if necessary, isolate clones containing the desired edit.

The HDR method was successfully used for targeting a specific modification in a coding sequence of a gene in plants (Budhagatapalli Nagaveni et al. 2015. "Targeted Modification of Gene Function Exploiting Homology-Directed Repair of TALEN-Mediated Double-Strand Breaks in Barley". G3 (Bethesda). 2015 September; 5 (9): 1857-1863). Thus, the gfp-specific transcription activator-like effector nucleases were used along with a repair template that, via HDR, facilitates conversion of gfp into yfp, which is associated with a single amino acid exchange in the gene product. The resulting yellow-fluorescent protein accumulation along with sequencing confirmed the success of the genomic editing.

Similarly, Zhao Yongping et al. 2016 (An alternative strategy for targeted gene replacement in plants using a dual-sgRNA/Cas9 design. Scientific Reports 6, Article number: 23890 (2016)) describe co-transformation of *Arabidopsis* plants with a combinatory dual-sgRNA/Cas9 vector that successfully deleted miRNA gene regions (MIR169a and MIR827a) and second construct that contains sites homologous to *Arabidopsis* TERMINAL FLOWER 1 (TFL1) for homology-directed repair (HDR) with regions corresponding to the two sgRNAs on the modified construct to provide both targeted deletion and donor repair for targeted gene replacement by HDR.

Activation of Target Genes Using CRISPR/Cas9.

Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components.

The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337:816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of CRISPR-associated endonuclease (Cas9) in conjunction with synthetic gRNAs can be used to produce targeted double-stranded brakes in a variety of different species.

The CRISPR/Cas9 system is a remarkably flexible tool for genome manipulation. A unique feature of Cas9 is its ability to bind target DNA independently of its ability to cleave target DNA. Specifically, both RuvC- and HNH-nuclease domains can be rendered inactive by point mutations (D10A and H840A in SpCas9), resulting in a nuclease dead Cas9 (dCas9) molecule that cannot cleave target DNA. The dCas9 molecule retains the ability to bind to target DNA based on the gRNA targeting sequence. The dCas9 can be tagged with transcriptional activators, and targeting these dCas9 fusion proteins to the promoter region results in robust transcription activation of downstream target genes. The simplest dCas9-based activators consist of dCas9 fused directly to a single transcriptional activator.

Importantly, unlike the genome modifications induced by Cas9 or Cas9 nickase, dCas9-mediated gene activation is reversible, since it does not permanently modify the genomic DNA.

Indeed, genome editing was successfully used to over-express a protein of interest in a plant by, for example, mutating a regulatory sequence, such as a promoter to overexpress the endogenous polynucleotide operably linked to the regulatory sequence. For example, U.S. Patent Application Publication No. 20160102316 to Rubio Munoz, Vicente et al. which is fully incorporated herein by reference, describes plants with increased expression of an endogenous DDA1 plant nucleic acid sequence wherein the endogenous DDA1 promoter carries a mutation introduced by mutagenesis or genome editing which results in increased expression of the DDA1 gene, using for example, CRISPR. The method involves targeting of Cas9 to the specific genomic locus, in this case DDA1, via a 20 nucleotide guide sequence of the single-guide RNA. An online CRISPR Design Tool can identify suitable target sites (www (dot) tools (dot) genome-engineering (dot) org. Ran et al. Genome engineering using the CRISPR-Cas9 system nature protocols, VOL. 8 NO. 11, 2281-2308, 2013).

The CRISPR-Cas system was used for altering gene expression in plants as described in U.S. Patent Application publication No. 20150067922 to Yang; Yinong et al., which is fully incorporated herein by reference. Thus, the engineered, non-naturally occurring gene editing system comprises two regulatory elements, wherein the first regulatory element (a) operable in a plant cell operably linked to at least one nucleotide sequence encoding a CRISPR-Cas system guide RNA (gRNA) that hybridizes with the target sequence in the plant, and a second regulatory element (b) operable in a plant cell operably linked to a nucleotide sequence encoding a Type-II CRISPR-associated nuclease, wherein components (a) and (b) are located on same or different vectors of the system, whereby the guide RNA targets the target sequence and the CRISPR-associated nuclease cleaves the DNA molecule, thus altering the expression of a gene product in a plant. It should be noted that the CRISPR-associated nuclease and the guide RNA do not naturally occur together.

In addition, as described above, point mutations which activate a gene-of-interest and/or which result in over-expression of a polypeptide-of-interest can be also introduced into plants by means of genome editing. Such mutation can be for example, deletions of repressor sequences which result in activation of the gene-of-interest; and/or mutations which insert nucleotides and result in activation of regulatory sequences such as promoters and/or enhancers.

Meganucleases-Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fokl.

Additionally Fokl has the advantage of requiring dimerization to have nuclease activity and this means the specificity increases dramatically as each nuclease partner recognizes a unique DNA sequence.

To enhance this effect, Fokl nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break.

Repair of these double-stranded breaks through the non-homologous end-joining (NHEJ) pathway most often results in small deletions or small sequence insertions. Since each repair made by NHEJ is unique, the use of a single nuclease pair can produce an allelic series with a range of different deletions at the target site.

The deletions typically range anywhere from a few base pairs to a few hundred base pairs in length, but larger deletions have successfully been generated in cell culture by using two pairs of nucleases simultaneously (Carlson et al., 2012; Lee et al., 2010).

In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENS on TALEs.

Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30 (5): 460-5; Miller et al. Nat Biotechnol. (2011) 29:143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"-involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type.

The end result is the introduction of the desired modification without the retention of any exogenous sequences.

The "double-replacement" or "tag and exchange" strategy-involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats.

Cre recombines the 34 base pair lox DNA sequence by binding to the 13 base pair inverted repeats and catalyzing strand cleavage and relegation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. December 1, (2003) 31 (23): 6873-6881].

Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred.

The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified.

Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells.

The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

Thus, according to some embodiments of the invention the pollen of the invention confers reduced fitness by way of partial genome incompatibility, parthenocarpy, stenospermocarpy, reduced shattering, inhibition of seed dormancy, cleistogamy, induced triploidy, conditional lethality, male sterility, female sterility, inducible promoters, complete sterility by nonflowering, reduced biotic/abiotic stress tolerance. The skilled artisan will know which method to select.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA.

Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant.

Micropropagation allows mass production of quality plant material in a short period of time and offers a rapid multiplication of selected cultivars in the preservation of the characteristics of the original transgenic or transformed plant.

The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced from the seedlings to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus.

Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Taylor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for case of constructing the desired viral vector with the foreign DNA. The virus can then be excised from the plasmid. If the virus is a DNA virus, a bacterial origin of replication can be attached to the viral DNA, which is then replicated by the bacteria.

Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters.

Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide.

Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Specific methods for weed transformation are described in Jofre-Garfias et al., 1997, Swain et al., 2010 and Pal et al., 2013, each of which is incorporated by reference in its entirety. According to a further aspect of the invention there is provided a method of producing pollen, the method comprising:

(a) growing weed producing pollen that reduces fitness of at least one weed species of interest; and (b) harvesting said pollen.

Thus the pollen product producing weed is grown in dedicated settings, e.g., open or closed settings, e.g., a greenhouse. According to a specific embodiment, the growth environment for the manufacture of the pollen does not include crop plants or the weed species of interest. For example, the growth area includes a herbicide susceptible weed variant but not a herbicide resistant weed variant (of the same species). Another example, the growth environment comprises a GM weed with a destructor gene said weed being fertile and producing pollen, but doesn't include the weed in which the destructor gene is expressed.

According to a specific embodiment, growing said weed producing pollen that reduces fitness is effected in a large scale setting (e.g., hundreds to thousands m$^2$).

According to some embodiments of the invention, the weed producing pollen comprises only male plants.

Harvesting pollen is well known in the art. For example, by the use of paper bags (Example 1). Another example is taught in US20060053686, which is hereby incorporated by reference in its entirety.

Once pollen is obtained it can be stored for future use. Examples of storage conditions include, but are not; limited to, storage temperatures in Celsius degrees e.g., −196, −160, −130, −80, −20, −5, 0, 4, 20, 25, 30 or 35; percent of relative humidity e.g., 0, 10, 20, 30, 40, 50, 60, 70, 80, 90 or 100. Additionally, the pollen can be stored in light or dark.

Alternatively, the pollen product of the present teachings is subjected to a post harvest treatment.

Thus, according to an aspect of the invention there is provided a method of producing pollen for use in artificial pollination, the method comprising:

(a) obtaining pollen that reduces fitness of at least one weed species of interest, e.g., as described herein; and (b) treating said pollen for use in artificial pollination.

Accordingly, there is provided a composition of matter comprising weed pollen that reduces fitness of at least one weed species of interest, said pollen having been treated for improving its use in artificial pollination.

Examples of such treatments include, but are not limited to coating, priming, formulating, chemical inducers, physical inducers [e.g., potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide], solvent solubilization, drying, heating, cooling and irradiating (e.g., gamma, UV, X-ray).

Additional ingredients and additives can be advantageously added to the pollen composition of the present invention and may further contain sugar, potassium, calcium, boron, and nitrates. These additives may promote pollen tube growth after pollen distribution on flowering plants.

In some embodiments, the pollen composition of the present invention contains dehydrated or partially dehydrated pollen.

Thus, the pollen composition may comprise a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, a herbicide or a pesticide.

Other ingredients and further description of the above ingredients is provided hereinbelow.

Under ordinary conditions of storage and use, the composition of the present invention may contain a preservative to prevent the growth of microorganisms.

The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Thus, pollen compositions that may also be used but not limited to mixtures with various agricultural chemicals and/or herbicides, insecticides, miticides and fungicides, pesticidal and biopesticidal agents, nematocides, bactericides, acaricides, growth regulators, chemosterilants, semiochemicals, repellents, attractants, pheromones, feeding stimulants or other biologically active compounds all of which can be added to the pollen to form a multi-component composition giving an even broader spectrum of agricultural protection.

Thus in the artificial pollination method of the present invention can be applied together with the following herbicides but not limited to: ALS inhibitor herbicide, auxin-like herbicides, glyphosate, glufosinate, sulfonylurcas, imidazolinones, bromoxynil, delapon, dicamba, cyclohezanedione, protoporphyrionogen oxidase inhibitors, 4-hydroxy-phenyl-pyruvate-dioxygenase inhibitors herbicides.

In some embodiments, the pollen can be combined with appropriate solvents or surfactants to form a formulation. Formulations enable the uniform distribution of a relatively small amount of the pollen over a comparatively large growth area. In addition to providing the user with a form of a pollen that is easy to handle, formulating can enhance its fertilization activity, improve its ability to be applied to a plant, enable the combination of aqueous-soluble and organic-soluble compounds, improve its shelf-life, and protect it from adverse environmental conditions while in storage or transit.

Numerous formulations are known in the art and include, but are not limited to, solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Solution formulations are designed for those active ingredients that dissolve readily in water or other non-organic solvents such as methanol. The formulation is a liquid and comprises of the active ingredient and additives.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Soluble powder formulations are similar to solutions in that, when mixed with water, they dissolve readily and form a true solution. Soluble powder formulations are dry and include the active ingredient and additives.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., Handbook of Insecticide Dust Diluents and Carriers, 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications.

In some embodiments of the disclosure, inactive ingredients i.e., adjuvants) are added to pollen to improve the performance of the formulation. For example, in one embodiment of the disclosure, pollen is formulated with a surfactant. A surfactant (surface active agent) is a type of adjuvant formulated to improve the dispersing/emulsifying, absorbing, spreading, and sticking properties of a spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis(2-chloroethyl)ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides (others are described hereinabove). Such carriers and additives may be used in solid, liquid, gas, or gel form, depending on the embodiment and its intended application.

As used herein "artificial pollination" is the application, by hand or dedicated machinery, of fertile stigmas with the pollen from plants with desired characteristics, as described herein.

Artificial pollination in the field can be achieved by pollen spraying, spreading, dispersing or any other method. The application itself will be performed by ground equipment, aircraft, unmanned aerial vehicles (UAV), remote-piloted vehicles (RPV), drones or specialized robots, special vehicles or tractors, animal assisted, specialized apparatus that is designed to spread boosts of pollen, specialized apparatus that combines ventilation and spraying of pollen to enhance recycling of pollen or any other application method or apparatus wherein application can be of a single dose, multiple doses, continuous, on an hourly/daily/weekly/monthly basis or any other application timing methodology.

Example 2 below (which is hereby incorporated into this section in its entirety) describes a number of embodiments for artificial pollination by hand, including:

(i) Direct application using paper bags;

(ii) Simple pollen dispersal above the female inflorescence (single application of total amount); or (iii) Continuous pollen spraying above the female inflorescence.

It will be appreciated that at any time the weed of interest can be further treated with other weed control means. For example, the weed may be treated with a herbicide (which is usually applied at early stages of germination as opposed to the pollen which is applied at flowering). Thus a herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

Thus, commercial products can be manufactured as kits whereby each pollen type is packed in a separate packaging means (e.g., bag), or two or more types of pollen are combined into a single composition and packed in a single packaging means (e.g., bag). The product may be accompanied by instructions for use, regulatory information, product description and the like.

The kit may also include in a separate packaging means other active ingredients such as at least one of a chemical inducer (as described above), herbicide, fertilizer, antibiotics and the like.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader.

All the information contained therein is incorporated herein by reference.

Example 1

Pollen Collection—Amaranthaceae, Poaceae, Asteraceae

Paper bags are used for pollen collection. Pollen is collected at morning (9:00 AM) by carefully inserting a male inflorescence into a paper bag and gently tapping the bag to release the pollen off the anthers. This collection process is repeated until pollen dust is visible inside the paper bags. Pollen grains are collected and pooled from multiple male plants. Each paper bag is weighed and the average pollen amount generated from a single male inflorescence and a single plant is calculated.

Example 2

Calibration of Pollen Amounts Needed for Optimal Pollination and Comparison Between Different Application Methods for Diecious Species—*Amaranthus palmeri, Amaranthus tuberculatus*

The experiment compares three pollen doses under four different application methods each group contains three female plants that are pollinated. In addition, one group of female plants is not pollinated at all and is used as control for apomixis levels. In all cases female plants are kept isolated from male plants. The doses that are used are approximately equivalent to pollen harvested from 0.1, 1, 10 total pollen of male plants, respectively. The application methods compared are: (i) Direct application using paper bags, (ii) Simple pollen dispersal above the female inflorescence (single application of total amount) (iii) Simple pollen dispersal above the female inflorescence (4 applications in intervals of 2 days, each application of 0.25 of the total amount of pollen dose) (iv) Continuous pollen spraying above the female inflorescence for 1 hour (the overall dose applied is identical to other treatments).

Pollen application by paper bags is conducted as follows: four paper bags with pollen and one paper bag without pollen are put on each of five flowering spikes randomly chosen. The spikes are longer than the paper bags, therefore, a label is attached just below the paper bag to mark the portion of the spike that is exposed to pollen. The paper bag with no pollen is used as a control.

Pollen application by simple pollen dispersal is conducted as follows: pollen is dispersed above the inflorescences of the female plants from 50 cm distance of the average female plant height. The pollen application process is repeated 4 times in application method iii.

Continuous pollen application by spraying is conducted from the same height as in application method ii for 1 hour.

14 days post pollination, seeds are harvested. In the paper bags method, the number of seeds per cm of spike is determined and in all other methods the number of seeds per female plant is determined.

TABLE 2

| Application method | Amount of pollen applied (as estimated from N male plants) | Single dose/ Multiple dose continuous application |
|---|---|---|
| Paper bags (i) | N = 0.1 | Single dose |
| Paper bags (i) | N = 1 | Single dose |
| Paper bags (i) | N = 10 | Single dose |
| Pollen dispersal (ii) | N = 0.1 | Single dose |
| Pollen dispersal (ii) | N = 1 | Single dose |
| Pollen dispersal (ii) | N = 10 | Single dose |
| Pollen dispersal (iii) | N = 0.1 | Multiple doses |
| Pollen dispersal (iii) | N = 1 | Multiple doses |
| Pollen dispersal (iii) | N = 10 | Multiple doses |
| Pollen spraying (iv) | N = 0.1 | Continuous |
| Pollen spraying (iv) | N = 1 | Continuous |
| Pollen spraying (iv) | N = 10 | Continuous |

Example 3

Calibration of Pollen Amounts Needed for Optimal Pollination and Comparison Between Different Application Methods for Monocious Species—*Lolium rigidum, Ambrosia trifida, Ambrosia artemisiifolia* and *Sorghum halepense*

This example is conducted similarly to Example 2 but rather instead of using female plants, all the male inflorescence on the pollinated plants are covered by paper bags in order to avoid self-pollination.

Example 4

Achieving Enhanced Susceptibility to Acetolactate Synthase (ALS) Inhibitors or EPSP Synthase Inhibitors by Pollen Application in Growth Rooms in *A. palmeri* and *A. tuberculatus*

*A. palmeri* resistant to ALS inhibitors seeds (Horak M J et al., 1997, Heap I, 2016) are germinated on soil and seedlings are transferred and transplanted into pots. When plants begin to flower, they are closely monitored daily to identify female plants at an early stage. Identified female plants are immediately transferred to another growth room to avoid being pollinated. Ten ALS resistant female plants are transferred into larger pots to allow full growth in size. 2 days after the transfer to large pots, female plants are divided into 2 groups of 5 female plants and each group is placed in a separate growth room having the same conditions and the plants continue to grow. At flowering time pollination procedure is conducted. In each separate room 5 female plants are pollinated by simple dispersal. In one room, the dispersed pollen was collected from males susceptible to ALS inhibitors (seeds obtained from Agriculture Research Service National Plant Germplasm System plant introduction as well as from various locations in Israel) and in the other room the dispersed pollen was collected from males resistant to ALS inhibitors. After 24 hours all the 10 female plants are transferred to the same room and seeds are harvested 14 days after the pollination event.

From each female plant, 100 seeds are taken and split into 2. Each set of 50 seeds are planted in trays of 15 by 15 cm. One tray is covered with a thin layer of soil before spraying the ALS inhibitor (ALS inhibitor—Atlantis, 2+10 g/L OD, Bayer is sprayed according to manufacturer instructions— 25+120 g/ha). Control trays are not sprayed. Emerging seedlings are counted 14 days after spraying. Emergence in control trays is used to estimate the potential total number of germinating seeds in sprayed trays of the same seed source. The proportion of resistance to ALS inhibitors is compared between the two progeny populations. The reduction in this proportion between the groups pollinated with resistant pollen and susceptible one reflects the effect of the susceptibility property that can be inherited by crossing these two specific susceptible and resistant varieties.

TABLE 3

| Female plants | Pollen source | Resistance estimation in progeny (as calculated from the number of seedlings that emerge out of 50 following herbicide application) |
|---|---|---|
| 5 resistant plants $F_R$ | Pollen from resistant plants $M_R$ | $N^R$ ($F_R \times M_R$) – Number of resistant seedlings |
| 5 resistant Plants $F_R$ | Pollen from susceptible plants $M_S$ | $N^R$ ($F_R \times M_S$) – Number of resistant seedlings |

Susceptibility inheritance = $1 - N^R (F_R \times M_S)/N^R (F_R \times M_R)$

A similar experiment is conducted using seeds from *A. palmeri* resistant to EPSP synthase inhibitors seeds (Culpepper A S et al. 2006, Heap I, 2016) where EPSPS inhibitor is used for selection (EPSPS inhibitor—ROUNDUP, 360 g/l SL, MONSANTO is sprayed according to manufacturer instructions—720 g/ha).

Separately, the experiment is repeated in an identical setup using *A. tuberculatus* resistant to ALS inhibitor seeds (Patzoldt W L et al., 2002, Heap I, 2016) or *A. tuberculatus* resistant to EPSP synthase inhibitors seeds (Vijay K. et al. 2013, Heap I, 2016). The source of susceptible seeds is from Agriculture Research Service National Plant Germplasm System plant introduction as well as from various locations in Israel.

Example 5

Achieving Enhanced Susceptibility to ALS or EPSPS Inhibitors by Pollen Application Under Competitive Conditions in Growth Rooms in *A. palmeri* and *A. tuberculatus*

*Palmeri* plants resistant to ALS inhibitors or EPSPS inhibitors (seeds source same as in Example 4) are grown and the separation between female and male plants is conducted as described in Example 4. At flowering time, two plots are being established, each of size 4×4 m, each containing together 5 females and 4 males plants. Both plots contain only resistant plants (both female and males). The two plots are located in separate growth rooms in order to avoid pollen cross contamination.

Pollen harvested from susceptible male plants is being dispersed on one of the plots and plants continue to grow for 14 days and then harvested. From each female plant, 100 seeds are collected and split into 2 sets. Each set of 50 seeds is planted in trays of 15×15 cm. One tray is covered with a thin layer of soil before spraying the ALS inhibitor or EPSPS inhibitor.

Control trays are not sprayed. Emerging seedlings are counted 14 days after spraying. Emergence in control trays is used to estimate the potential total number of germinating seeds in sprayed trays of the same seed source.

The proportion of resistance to ALS inhibitors or EPSPS inhibitors is compared between the progeny population originated from the two plots with and without the additional susceptible pollen. The enhanced susceptibility to ALS inhibitors or EPSPS inhibitors between the plots with the artificial pollination relatively to the one without it shows the efficacy of the artificial pollination under competitive conditions.

TABLE 4

| Female plants | Pollen source | Resistance estimation in progeny (as calculated from the number of seedlings emerge out of 50 following herbicide application) |
|---|---|---|
| 5 resistant plants $F_R$ | 5 resistant plants $M_R$ | $N^R$($F_R$x$M_R$) – Number of resistant seedlings |
| 5 resistant Plants $F_R$ | 5 Resistant plants + pollen from susceptible plants $M_R + M_s$ | $N^R$($F_R$x($M_R + M_s$)) – Number of resistant seedlings |

Efficacy of the artificial pollination under competitive conditions = $1 - N^R(F_R X(M_R + M_s))/N^R(F_R xM_R)$

Example 6

Achieving Enhanced *Lolium rigidum* Susceptibility to ALS/ EPSPS Inhibitor by Pollen Application in Growth Rooms

*L. rigidum* resistant to ALS inhibitor or EPSPS inhibitor seeds (Matzrafi M and Baruch R, 2015) are germinated on soil and seedlings are transferred and transplanted into pots. The experiment is conducted as described in Example 4.

Example 7

Achieving Enhanced *Ambrosia artemisiifolia* (Common Ragweed) Susceptibility to ALS/EPSPS Inhibitor by Pollen Application Under Competitive Conditions in Growth Rooms

*A. artemisiifolia* resistant to EPSPS inhibitor seeds (Heap I, 2016) is germinated on soil and seedlings are transferred and transplanted into pots. Ten female plants are taken and divided into two groups of 5. Each group is placed in separate growth rooms with similar conditions to avoid cross-pollination. When plants begin to flower, one group is being artificially pollinated by dispersal of pollen harvested from male plants susceptible to EPSPS inhibitor while the other group is not artificially pollinated.

As the *Ambrosia* species is monoecious, the artificial pollination that is conducted here is under competitive conditions as native pollen exists at the flowering period. Seeds are harvested 14 days after the pollination event.

From each female plant, 100 seeds are collected and split into 2 sets. Each set of 50 seeds is planted in trays of 15×15 cm. One tray is covered with a thin layer of soil before spraying with ALS/EPSPS inhibitor. (ALS inhibitor—Atlantis, 2+10 g/L OD, Bayer is sprayed according to manufacturer instructions—25+120 g/ha, EPSPS inhibitor—ROUNDUP, 360 g/l SL, MONSANTO is sprayed according to manufacturer instructions—720 g/ha).

Control trays are not sprayed but are only covered with a thin layer of soil. Emerging seedlings are counted 14 days after spraying. Emergence in control trays is used to estimate the potential total number of germinating seeds in sprayed trays of the same seed source. The proportion of resistance to ALS/EPSPS inhibitor is compared between the two progeny populations. The reduction in this proportion between the groups pollinated with susceptible pollen and the one not artificially pollinated reflects the efficacy of the pollination treatment in monoecious species such as ambrosia.

TABLE 5

| # of plants | Pollen source (native/external) | Resistance estimation in progeny (as calculated from the number of seedlings emerge out of 50 following herbicide application) |
|---|---|---|
| 5 resistant plants (R) | Native pollen only (R) | $N^R$(RxR) – Number of resistant seedlings |
| 5 resistant Plants (R) | Native pollen (R) + external application (S) | $N^R$(Rx(R + S)) – Number of resistant seedlings |

Efficacy of treatment for susceptibility inheritance = 1 – $N^R$(Rx(R + S))/$N^R$(RxR)

Example 8

Achieving Enhanced *Ambrosia trifida* (Giant Ragweed) Susceptibility to ALS/EPSPS Inhibitor by Pollen Application Under Competitive Conditions in Growth Rooms Experiment is conducted and evaluated as described in Example 7 with *Ambrosia trifida* instead of *Ambrosia artemisiifolia*.

Example 9

Generation and Evaluation of a "Super Herbicide Sensitive" Weed by Breeding of *A. palmeri, A. tuberculatus*

To produce super herbicide sensitive pollen from *A. palmeri* the following selection for highest sensitivity to various herbicides was performed:

1. *A. palmeri* line with highest sensitivity to EPSP synthase inhibitors mode of action was first picked in the following way: application of EPSPS inhibitor at 0.125×, 0.25×, 0.5×, 1× and 2×, where × is the standard recommended levels of glyphosate. Clones of plants that died from 0.125× were allowed to produce seed and were further subjected to recurrent selection to generate the most sensitive plants (S lines), which died from 0.125× glyphosate.

2. *A. palmeri* with highest sensitivity to ALS inhibitors mode of action was picked by application of ALS inhibitor at 0.125×, 0.25×, 0.5×, 1× and 2×, where × is the standard recommended levels of ALS inhibitor. Clones of plants that died from 0.125× were allowed to produce seed and were further subjected to recurrent selection to generate the most sensitive plants (S lines), which died from 0.125×ALS inhibitor. 3. *A. palmeri* with highest sensitivity to Acetyl CoA Carboxylase (ACCase) inhibitors mode of action was picked by application of ACCase inhibitor at 0.125×, 0.25×, 0.5×, 1× and 2×, where × is the standard recommended levels of ACCase inhibitor. Clones of plants that died from 0.125× were allowed to produce seed and were further subjected to recurrent selection to generate the most sensitive plants (S lines), which died from 0.125× ACCase inhibitor.

The *A. palmeri* lines obtained by the methods described herein may be further crossed by traditional breeding techniques to obtain a plant weed line that is "Super herbicide sensitive" to multiple modes of actions.

Evaluation of enhanced *A. palmeri* susceptibility to EPSP synthase inhibitors, ALS inhibitors and Acetyl COA Carboxylase (ACCase) inhibitors by pollen application in growth rooms is conducted as described in Example 4 with the usage of multiple herbicides instead of one herbicide.

The same procedure to obtain "super herbicide sensitive" is done with *A. tuberculatus*.

Example 10

Generation and Evaluation of the Sterility Property of *A. palmeri* or *A. tuberculatus* Transformed with "Terminator Technology" Genes As previously described in U.S. Pat. No. 5,925,808, 3 plasmids are being used for *A. palmeri* or A. tubercultus transformation.

1. a gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to a repressible promoter.

3. A third gene that encodes the repressor specific for the repressible promoter.

Plasmid sequences and procedures are used as described in U.S. Pat. No. 5,925,808, supra:

1. The death gene used is RIP (ribosomal inactivating protein, sequence of a complete RIP gene, saporin 6: GenBank ID SOSAP6, Accession No. X15655) or barnase (Genbank Accession M14442)

2. Construction of a CRE Gene under the control of a Tetracycline-derepressible 35S Promoter.

3. Third plasmid is Tet Repressor Gene Driven by a 35S Promoter.

The transiently active promoter in the first plasmid is replaced with *A. palmeri* promoter or *A. tuberculatus* that is expressed during embryogenesis, seed development or seed germination. *A. palmeri* or *A. tuberculatus* transformation is carried out as previously described in Pal A., et al 2013. A stably transformed line that highly expresses the desired plasmids is picked for further stages.

Seeds from this *A. palmeri* or *A. tuberculatus* line are split into two groups: one group is treated with tetracycline whereas the other group is left untreated. The plants are grown and identified males from each group are picked for the evaluation stage.

Evaluation of the efficiency of sterility in the transformed line is conducted in the following way: Two plots are being established at flowering time: 1. Containing 5 natural female *A. palmeri* or *A. tuberculatus* plants with 4 males from this transformed line that are not treated with tetracycline in the seed stage. 2. Containing 5 natural female *A. palmeri* or *A. tuberculatus* plants with 4 males from this genetically modified line that is treated with tetracycline in the seed stage. Plants continue to grow for 14 days and then seeds are being harvested. Two measures are being estimated: 1. Total count and weight of seeds produced from each female plant where the difference between the counts and weights between the two groups represent sterility efficiency. 2. From each female plant 50 seeds are taken and planted and the number of emerged seedlings is counted at the age of 14 days. The sterility efficiency is estimated from these two parameters.

TABLE 6

| plants | Pollen source | Seeds count and weight | Seedling emergence estimation in progeny (as calculated from the number of seedlings emerge out of 50) |
|---|---|---|---|
| 5 female plants F | 5 males with the "terminator technology" without tetracycline treatment $M_{T\text{-}tet}$ | $N_{seeds}$(Fx $M_{T\text{-}tet}$) – seed count $W_{seeds}$(Fx $M_{T\text{-}tet}$) – total seed weight | $N_{seedlings}$(Fx $M_{T\text{-}tet}$) – Number of seedlings |
| 5 female plants F | 5 males with the "terminator technology" with tetracycline treatment $M_{T+tet}$ | $N_{seeds}$(Fx $M_{T+tet}$) – seed count $W_{seeds}$(Fx $M_{T+tet}$) – total seed weight | $N_{seedlings}$ (Fx $M_{T+tet}$) – Number of seedlings |

Efficacy of Sterility by number of seeds or seedlings = 1 – (N(Fx $M_{T+tet}$)/N(Fx $M_{T\text{-}tet}$))

An alternative set of plasmids that are used are based on the Tet ON system in which the rtTA (reverse tetracycline controlled transactivator) protein is capable of binding the operator only if bound by a tetracycline and as a consequence activates transcription:

1. a gene which expression results in an altered plant phenotype linked to a transiently active promoter, the gene and promoter being separated by a blocking sequence flanked on either side by specific excision sequences.

2. A second gene that encodes a recombinase specific for the specific excision sequences linked to an operator that is upstream to the promoter and is responsive to an activator.

3. A third gene that encodes the activator specific for the operator in the second plasmid. Under one instance the activator can be regulated by an inducible promoter. Alternatively, the inducer can bind the activator protein eliciting a conformational change to its active form.

Plasmid sequences are:

1. The death gene used is RIP (ribosomal inactivating protein, sequence of a complete RIP gene, saporin 6: GenBank ID SOSAP6, Accession No. X15655) or barnase (Genbank Accession M14442) under the control of a specific embryogenesis, seed development or germination promoter.

2. Construction of a CRE Gene under the control of a Tetracycline-responsive element (TRE).

3. Third plasmid is a 35S promoter upstream of a fusion of a Tet Repressor Gene, reverse TetR (reverse tetracycline repressor), found in *Escherichia coli* bacteria, with the activation domain of another protein, VP16, found in the Herpes Simplex Virus (termed rtTA).

Upon application of tetracycline or its derivatives such as doxycycline the rtTA becomes activated and results in expression of the CRE recombinase and consequently activation of the death gene.

Another set of plasmids that are used is based on only two sets of plasmids:

1. a gene which expression results in an altered plant phenotype linked to a transiently active promoter and an operator that is upstream to the promoter and is responsive to an activator.

2. A second gene that encodes the activator specific for the operator from the first plasmid which is activated upon induction. Plasmid sequences are:

1. The death gene used is RIP (ribosomal inactivating protein, sequence of a complete RIP gene, saporin 6: GenBank ID SOSAP6, Accession No. X15655) or barnase (Genbank Accession M14442) under the control of a a specific embryogenesis, seed developmentor germination promoter and upstream to the promoter a TRE sequences.

2. A constitutive promoter upstream of a rtTA gene.

Upon application of tetracycline or its derivatives such as doxycycline the rtTA becomes activated and results in activation of the death gene.

Similar experimental setups are repeated with both plasmid sets explained above and the efficiency of sterility is calculated and evaluated as explained with the first plasmid set.

Example 11

Generation and Evaluation of the Sterility Property in *A. palmeri* or *A. tuberculatus* Transformed with Sterility Genes Under Specifically Regulated Promoter

*A. palmeri* or *A. tuberculatus* sterile line is being produced using 2 plasmids:

1. Plasmid encoding for a disrupter protein under a promoter that is active in the embryo or seed, which makes it sterile where the gene promoter is under the control of a specific operator sequence responsive to repression by a repressor protein.

2. A repressor protein, whose gene is under the control of a constitutive promoter. When binding to a specific chemical the repressor can bind the operator from the first plasmid and inhibit the expression of the disrupter protein. Plasmid sequences are:

1. RIP gene (ribosomal inactivating protein, sequence of a complete RIP gene, saporin 6: GenBank ID SOSAP6, Accession No. X15655) or barnase (Genbank Accession M14442) under the control of a specific embryogenesis, seed development or germination promoter with a TetO that is responsive to reverse tetracycline repressor.

2. Construction of a reverse tetracycline repressor gene under the control of a constitutive promoter.

Upon tetracycline application the reverse tetracycline repressor binds tetracycline and leads to repression of disrupter gene.

Evaluation of the efficiency of sterility in the transformed line is conducted as described in Example 10. The evaluation includes two stages:

1. Comparing the total seed number and weight between the groups.

2. Comparing the fraction of emerged seedlings out of 50 seeds sown. The experimental setup for the second stage is illustrated in the table below:

TABLE 7

| Female plants | Pollen source | Seeds count and weight | Seedling emergence estimation in progeny (as calculated from the number of seedlings emerge out of 50) |
|---|---|---|---|
| 5 female plants F | 5 males of the transformed line without tetracycline treatment $M_{T\text{-}tet}$ | $N_{seeds}$(Fx $M_{T\text{-}tet}$) – seed count $W_{seeds}$(Fx $M_{T\text{-}tet}$) – total seed weight | $N_{seedlings}$ (Fx $M_{T\text{-}tet}$) – Number of seedlings |
| 5 female plants F | 5 males of the transformed line with tetracycline treatment $M_{T+tet}$ | $N_{seeds}$(Fx $M_{T+tet}$) – seed count $W_{seeds}$(Fx $M_{T+tet}$) – total seed weight | $N_{seedlings}$ (Fx $M_{T+tet}$) – Number of seedlings |

Efficacy of Sterility by number of seeds or seedlings = $1 - N$(Fx $M_{T\text{-}tet}$)/$N$(Fx $M_{T+tet}$)

An alternative set of plasmids that are used are based on the Tet OFF system:

1. Plasmid encoding for a disrupter protein under a promoter that is active in the embryo or seed, which makes the plant sterile where the gene promoter is under the control of a specific operator sequence responsive to activation by an activator protein.

2. An activator protein, whose gene is under the control of a constitutive promoter. Upon specific chemical binding to this activator it becomes non-active and can no longer activate the transcription of the first plasmid.

Plasmid sequences are:

1. RIP gene (ribosomal inactivating protein, sequence of a complete RIP gene, saporin 6: GenBank ID SOSAP6, Accession No. X15655) or barnase (Genbank Accession M14442) under the control of a dual regulation with a specific embryogenesis, seed developmentor germination promoter and a TRE sequence.

2. Construction of a tetracycline transactivator protein tTA gene (composed of fusion of one protein, TetR (tetracycline repressor), found in *Escherichia coli* bacteria, with the activation domain of another protein, VP16 under the control of a constitutive promoter.

Upon application of tetracycline or its derivatives such as doxycycline the tTA becomes repressed and results in loss of activation of the disrupter gene and recovery of sterility.

Similar experimental setups are repeated with this plasmid set and the efficiency of sterility is calculated and evaluated as explained with the first plasmid set.

Example 12

Generation and evaluation of the susceptibility to EPSPS inhibitor in *A. palmeri* or *A. tuberculatus* transformed with antisense RNA under specifically regulated promoter As in Example 10 with the use of an antisense RNA against EPSP synthase replacing the disrupter gene. EPSP synthase antisense sequence that is conserved across multiple *Amaranthus* species is used, e.g., corresponding to nucleotide positions 590-802 (antisense) of KF5692111.

Induced EPSPS inhibitor susceptibility will be examined following application of both tetracycline for activation of EPSPS antisense expression and application of EPSPS inhibitor (ROUNDUP, 360 g/l SL, MONSANTO is sprayed according to manufacturer instructions-720 g/ha) for selection.

Example 13

Generation of *A. palmeri* or *A. tuberculatus* Sterile Hybrid Line Transformed with Dual Complementary Male and Female Plant Genetic Recombinations Systems

*A. palmeri* or *A. tuberculatus* sterile line is being produced by crossing between two homozygous transformed plants. The male and female plants are each transformed with a plasmid encoding a disrupter gene controlled by a transiently active promoter, the gene and promoter being separated by a blocking sequence flanked on either side by specific excision sequences (such as lox or frt excision sequences). In addition the plasmid contains a second gene that encodes a genetic recombination enzyme (such as cre recombinase or flp flippase) specific for the excision sequences in the opposite sex (namely, the recombination enzyme of the female plant cut the excision sequence in the male and vice versa). These recombination enzymes are under the control of a promoter that is active post seed germination stage. The transformed plasmid both in the male and in the female homozygous lines are inserted to the same genomic locus position.

The following plasmid is transformed into the female plant:

Plasmid encoding a barnase or RIP gene under the control of a specific embryogenesis or germination promoter whereas the gene and promoter being separated by a blocking sequence flanked on either side by specific excision lox sequences and a second gene encoding for a flippase recombination enzyme under a promoter that is active post seed germination.

The following plasmid is transformed into the male plant:

Plasmid encoding a barnase or RIP gene under the control of a specific embryogenesis or germination promoter whereas the gene and promoter are being separated by a blocking sequence flanked on either side by specific excision frt sequences and a second gene encoding for a cre recombinase recombination enzyme under a promoter that is active post seed germination.

Lines are being selected such that both insertions to both male and female are on the exact same genomic position.

Only upon crossing between these male plants with these female plants both recombination events by flp and cre are occurring thus yielding pollen that have a barnase or RIP gene under the control of a specific embryogenesis or germination promoter.

Example 14

Evaluation of the Sterility Property in *A. palmeri* or *A. tuberculatus* Hybrid Line Transformed with Dual Complementary Male and Female Plant Recombinase/Flippase Systems Evaluation of the efficiency of sterility in the transformed line is conducted as described in Example 10. The evaluation includes 2 stages: 1. Comparing the total seed number and weight between the two compared groups 2. Comparing the fractions of emerged seedlings out of 50 seeds sown. The experimental setup is illustrated in the table below:

TABLE 8

| Female plants | Pollen source | Seeds count and weight | Seedling emergence estimation in progeny (as calculated from the number of seedlings emerge out of 50) |
|---|---|---|---|
| 5 female plants F | 4 natural male plants M | $N_{seeds}$(FxM) – seed count $W_{seeds}$(Fx M) – total seed weight | $N_{seedlings}$(FxM) – Number of seedlings |
| 5 female plants F | 4 hybrid male plants $M_{hyb}$ | $N_{seeds}$(Fx $M_{hyb}$) – seed count $W_{seeds}$(Fx $M_{hyb}$) – total seed weight | $N_{seedlings}$ (Fx$M_{hyb}$) – Number of seedlings |

Efficacy of Sterility by number of seeds or seedlings = 1 – (N(Fx$M_{hyb}$)/N(Fx M))

Example 15

Achieving Reduction of *A. palmeri* or *A. tuberculatus* Population by Application of Sterile Pollen in Growth Room

*A. palmeri* or *A. tuberculatus* seeds are germinated on soil and seedlings are transferred and transplanted into pots. At flowering time two plots are being established, each of size 4×4 m, each containing together 5 female and 4 male plants.

The two plots are located in separated growth rooms in order to avoid pollen cross contamination. Sterile pollen generated as described in Example 10, 11 or 13 is dispersed on one of the plots. The application procedure is one application per day for 5 consecutive days. The plants continue to grow for 14 days and then harvested. Seed biomass is measured for each plant and the number of seeds per 0.1 g is being counted and the total number of seeds per plant is being estimated and recorded. In addition, from each female plant, 100 seeds are taken. The seeds are planted in trays of 30×30 cm. Emerged seedlings are counted at the age of 14 days and the emergence rate is calculated for both groups. The reduction in the emergence proportion between the group pollinated with sterile pollen and the control group reflects the estimation for the reduction in *A. palmeri* or *A. tuberculatus* population size due to the treatment per one reproduction cycle.

TABLE 9

| Female plants | Pollen source | Seeds count and weight | Population size reduction estimation (as calculated from the number of seedlings emerge out of 100 seeds) |
|---|---|---|---|
| 5 female plants | 4 male plants | $N_{seeds}$(FxM) – seed count $W_{seeds}$(FxM) – total seed weight | N (FxM) – Number of emerged seedlings |
| 5 female Plants | 4 male plants + sterile pollen | $N_{seeds}$(Fx(M + $M_s$)) – seed count $W_{seeds}$(Fx(M + $M_s$)) – total seed weight | N (Fx(M + $M_s$)) – Number of emerged seedlings |

Expected population size reduction per year = 1 – N (Fx(M + $M_s$))/N (FxM)

Example 16

Achieving Reduction of *A. palmeri* or *A. tuberculatus* Population by Application of Sterile Pollen in Controlled Field Conditions Sterile pollen is generated as described in Example 10, 11 or 13 and collected as described in Example 1. Two groups of 8 *A. palmeri* plants composed of 4 male plants and 4 female plants are transplanted in the field. Each group is arranged in 2 rows of four plants in alternating order of female and male. The distance between each plant is 1m. The distance between the location of the 2 groups is 1 km. The two groups are treated similarly and are watered on a daily basis. One group is used as control group (C) to estimate the native population growth without any application of non-native pollen. The second group (T) is pollinated both with the native pollen and with additional sterile pollen that was generated as described in Examples 10, 11, or 13. At the beginning of the flowering time a pollination treatment is being applied to group T. The treatment is given in 4 applications in intervals of 3 days, each application is given once a day (at morning hours). All plants are harvested after seed maturation and seeds are being collected manually. Seed biomass is measured for each plant and the number of seeds per 0.1 g is being counted and the total number of seeds per plant is being estimated and recorded.

In addition, from each female plant, 100 seeds are taken. The seeds are planted in trays of 30×30 cm. Emerged seedlings are counted at the age of 14 days and the emergence rate is calculated for both groups. The reduction in the emergence proportion between the group pollinated with sterile pollen and the control group reflects the estimation for the reduction in *A. palmeri* or *A. tuberculatus* population size due to the treatment per one year.

TABLE 10

| Female plants | Pollen source | Seeds count and weight | Population size reduction estimation (as calculated from the number of seedlings emerge out of 100 seeds) |
|---|---|---|---|
| 4 female plants | 4 male plants | $N_{seeds}$(FxM) – seed count $W_{seeds}$(FxM) – total seed weight | N (FxM) – Number of emerged seedlings |
| 4 female Plants | 4 male plants + sterile pollen | $N_{seeds}$(Fx(M + $M_s$)) – seed count $W_{seeds}$(Fx(M + $M_s$)) – total seed weight | N (Fx(M + $M_s$)) – Number of emerged seedlings |

Expected population size reduction per year = 1 – N (Fx(M + $M_s$))/

Example 17

Achieving Reduction of *A. palmeri* or *A. tuberculatus* Population by Application of Sterile Pollen from a Natural Seedless Strain in Growth Room Pollen is collected from naturally occurring seedless strain of *A. palmeri* or *A. tuberculatus*. This pollen is used as described in Example 15 to evaluate the efficacy of the sterility achieved.

Example 18

Achieving Sterility in *A. palmeri* or *A. tuberculatus* by Applying Pollen Harvested from Tetraploid A. Palmer Strain Generation of *A. palmeri* or *A. tuberculatus* tetraploid plants is achieved by treatment of 0.25% aqueous solution of colchicine on growing buds of seedling thrice daily for three consecutive days. Pollen from these plants is harvested and collected.

This pollen is used as described in Example 15 to evaluate the efficacy of the sterility achieved.

Example 19

Achieving Sterility in *A. palmeri* or *A. tuberculatus* by Applying Pollen Pre-Treated with Irradiation Pollen from naturally occurring *A. palmeri* or *A. tuberculatus* plants is harvested and collected. The pollen is treated by UV, X-ray or gamma irradiation. This pollen is used as described in Example 15 to evaluate the efficacy of the sterility achieved.

Example 20

Achieving Reduction of *A. palmeri* and *A. tuberculatus* Populations by Application of Mixture of Sterile Pollen in a Controlled Field Conditions Sterile pollen is generated as described in Examples 10, 11, 13, 17, 18 or 19 and collected as described in Example 1 both from *A. palmeri* male plants and from *A. tuberculatus* male plants. The pollen from both species is mixed together and the treatment is with this mixture. The field experimental setup is similar to the one described in Example 16 except that instead of having in each group 8 *A. palmeri* plants (composed of 4 female and 4 males plants) each group contains 4 *A. palmeri* plants (2 females and 2 males) and 4 *A. tuberculatus* plants (2 females and 2 males). At the beginning of flowering time one group is being treated with the pollen mixture 1 application per day for 4 times in intervals of 3 days.

The effect of pollen treatment on the population size of both species is estimated similarly to the way described in example 16.

TABLE 11

| Female plants | Pollen source | Population size reduction estimation (as calculated from the number of seedlings emerge out of 100 seeds) |
|---|---|---|
| 2 *A. palmeri* + 2 *A. tuberculatus* | 2 *A. palmeri* + 2 *A. tuberculatus* | $N_p$ (FxM) – Number of *A. palmeri* emerged seedlings $N_t$ (FxM) – Number of *A. tuberculatus* emerged seedlings |
| 2 *A. palmeri* + 2 *A. tuberculatus* | 2 *A. palmeri* + 2 *A. tuberculatus* + mixture of sterile pollen | $N_p$ (Fx(M + $M_s$)) – Number of *A. palmeri* emerged seedlings $N_t$ (Fx(M + $M_s$)) – Number of *A. tuberculatus* emerged seedlings |

Expected population size reduction per year = $1 - N_{p/t}$ (Fx(M + $M_s$))/$N_{p/t}$ (FxM)

Example 21

Generation and Evaluation of Induced EPSPS Inhibitor Susceptibility Following *A. Palmeri* or *A. tuberculatus* Transformation with AlcR Based Ethanol Inducible Death Gene

*A. palmeri* or *A. tuberculatus* EtoH inducible line is being produced using a plasmid encoding for AlcR based EtoH inducible promoter linked to a barnase gene or a RIP gene. In this example there is no repression or tissue specific promoter. The promoter is activated after EtoH spraying and therefore, the seeds do not develop.

*A. palmeri* transformation is carried out as previously described in Pal A., et al 2013 to *A. tricolor*, supra. A stable transformed line that highly expresses the desired plasmids is selected for further stages.

Pollen collected from this line are examined in a similar protocol as explained in Example 4 except that seeds are sprayed with EtoH instead of the herbicide used in that example to evaluate the efficiency of death following EtoH application.

Example 22

Generation and Evaluation of Induced Death Following *A. palmeri* or *A. Tuberculatus* Transformation with AlcR Based Ethanol Inducible EPSPS Antisense RNA As in Example 21 with the use of an antisense RNA against EPSP synthase replacing the disrupter gene. EPSP synthase antisense sequence that is conserved across multiple *Amaranthus* species is used, e.g., corresponding to nucleotide positions 597-809 (antisense) of FJ861243.1.

Induced EPSPS inhibitor susceptibility will be examined following application of both EtOH for activation of EPSPS antisense expression and application of EPSPS inhibitor (ROUNDUP, 360 g/l SL, MONSANTO is sprayed according to manufacturer instructions-720 g/ha) for selection.

Example 23

Demonstration of Seed Production Via Artificial Pollination in *A. palmeri*

*A. palmeri* seeds were germinated on paper and the seedlings were transferred into small pots. After the plants reached a height of about 20 cm they were transferred again into larger pots. When plants began flowering, they were closely monitored daily to identify their sex at an early stage. Immediately after sex identification the females and males were separated and placed in different locations (~6 m apart) outside on September-October in Israel.

Pollen was collected at early morning from *A. palmeri* male plants using paper tubes (12 cm in length and a diameter of ~1 cm). Each such paper tube was placed on a single male spike. Pollen was released by gently tapping on the paper tube. Each paper tube was used to pollinate an *A. palmeri* female spike by placing it (with the pollen inside) on one spike and gently tapping it (tapping procedure was repeated several times at intervals of ~10 minutes to enhance pollination). The procedure of artificial pollination was repeated for several days (2-3 times) for each spike and the entire experiment was repeated 3 times—overall 8 spikes (first experiment—2 spikes, second experiment—2 spikes, third experiment—4 spikes were pollinated and 7 spikes served as controls with no application of pollen (first experiment—2 spikes, second experiment—2 spikes, third experiment—3 spikes). The total number of seeds formed (15-20 days post initial pollination event) from each spike and their weights were measured and the results are depicted in Table 12 below:

TABLE 12

| # Exp | # of control spikes | # of pollinated spikes | Control seeds Avg. sample weight (g) | Pollinated seeds Avg. sample weight (g) | Fold Change Pollinated/ Control | P-value |
|---|---|---|---|---|---|---|
| 1 | 2 | 2 | 0.07 | 0.18 | 2.52 | 0.06 |
| 2 | 2 | 2 | 0.05 | 0.14 | 2.77 | 0.15 |
| 3 | 3 | 4 | 0.041 | 0.145 | 3.67 | 0.0078 |
| Combined data | 7 | 8 | 0.052 | 0.155 | 2.96 | 2.36E-5 |

As can be seen from the table artificial pollination significantly increase the amount of seeds formed.

To evaluate the quality of the seeds that were obtained, average seed weight was calculated and compared to average seed weight of seeds that were collected directly from the field. Results demonstrated that natural seeds and seeds obtained from artificial pollination had a similar weight (see FIG. 1).

Example 24

Inhibition of Seed Development and Demonstration of Weed Control by Reduced Seed Germination in *A. palmeri* by Applying X-Ray Irradiated Pollen in Growth Room

*A. palmeri* seeds were germinated on paper and the seedlings were transferred into small pots. After the plants reached a height of about 20 cm they were transferred into larger pots. When plants began flowering, they were closely monitored daily to identify their sex at an early stage. Immediately after sex identification the females and males were separated and placed in different growth rooms in order to avoid pollination. One female plant with relatively many flowering spikes was transferred into a growth chamber (conditions of 30°/22° C., photoperiod 16/8 day/night) where the pollination experiment was conducted.

Pollen was collected at early morning from *A. palmeri* male plants using paper tubes (12 cm in length and a diameter of ~1 cm). Each such paper tube was placed on a single male spike. Pollen was released by gently tapping on the paper tube. Eight such paper tubes with fresh pollen were collected and divided into two sets of 4. Each set of 4 paper tubes was placed in a 15 cm petri dish. One petri dish was irradiated by X-ray radiation of 300 Gy (overall the duration of the radiation was 80 minutes) while the other petri dish was placed for that time in similar conditions only without radiation and served as a control with non-irradiated pollen. About 2 hours after pollen collection it was used to artificially pollinate 8 spikes of a female *A. palmeri* plant. These 8 spikes were divided into 4 pairs where the height of the branch origin of each such pair was approximately the same. Each paper tube was used to pollinate an *A. palmeri* female spike by placing it (with the pollen inside) on one spike and gently tapping it (tapping procedure was repeated several times in intervals of ~15 minutes to enhance pollination). Pollination was conducted such that one spike from each pair was pollinated with the irradiated pollen and the other with non-irradiated pollen (overall 4 pairs were pollinated). Additional 2 empty paper tubes with no pollen inside were placed on additional 2 spikes in order to serve as a "no-pollen" control. The paper tubes were removed from the spikes after about an hour. 18 days after pollination the top 12 cm of each of the 10 spikes was cut and seeds were harvested. Total seed weight and total seed count per spike were measured and seed morphology was examined.
The results are depicted in Table 13, below.

TABLE 13

| Sample | Total Seed Weight (gr) | Number of Seeds | Average Seed Weight (mgr) |
|---|---|---|---|
| Regular pollen #1 | 0.0769 | 214 | 0.359 |
| Regular pollen #2 | 0.0777 | 221 | 0.352 |
| Regular pollen #3 | 0.0936 | 317 | 0.295 |
| Regular pollen #4 | 0.0589 | 227 | 0.259 |
| Irradiated pollen #1 | 0.0173 | 181 | 0.096 |
| Irradiated pollen #2 | 0.0193 | 183 | 0.105 |
| Irradiated pollen #3 | 0.0152 | 134 | 0.113 |

TABLE 13-continued

| Sample | Total Seed Weight (gr) | Number of Seeds | Average Seed Weight (mgr) |
|---|---|---|---|
| Irradiated pollen #4 | 0.0067 | 105 | 0.064 |
| No-pollen | 0.0011 | 1 | NA |
| No-pollen | 0 | 0 | NA |
| Average value for regular pollen | 0.076775 | 244.75 | 0.316417252 |
| Average value for irradiated pollen | 0.014625 | 150.75 | 0.094571738 |
| t-test p-value | 0.00018 | 0.022 | 0.00015 |

Figures 1, 2:
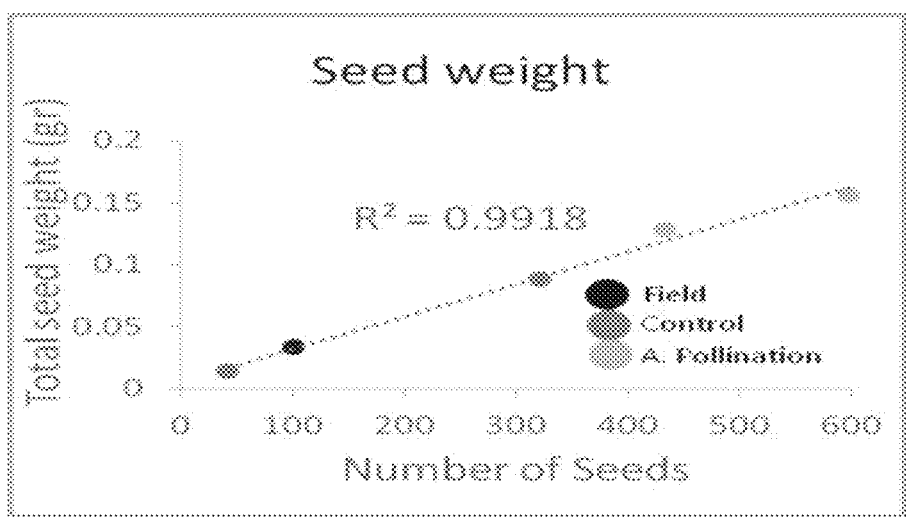
FIG. 1 is a graph showing that the weight of seed obtained by artificial pollination is equivalent to that of seeds collected from the field or obtained by natural pollination.
FIG. 2 is an image showing inhibition of seed development demonstrated by comparing the appearance of random assortment of seeds generated by artificial pollination with X-ray irradiated pollen vs. non-irradiated pollen.

Seeds were examined under the microscope and for each sample pictures were taken for a random assortment of seeds with representative appearance (See FIG. 2). In general, the seeds obtained from the artificial pollination with the irradiated pollen looked thin, partly empty and their color was light brown while the ones obtained from the regular pollen looked more filled having a darker brown/black color.

Germination assay was conducted in order to estimate the different germination levels between the seeds obtained by artificial pollination with the irradiated pollen versus the ones obtained from artificial pollination with regular pollen.

Thirty seeds were taken from each of these 8 samples. Each set of 30 seeds was placed in a 6 cm petri dish on a towel paper with 7.5 ml tap water for the germination test. These petri dishes were sealed with parafilm and were placed in a growth chamber in 34/25° C. 16/8h day/night conditions for 16 days. After 16 days emerged seedlings were counted and germination rate was calculated for each sample. A comparison was conducted between the seeds obtained from irradiated pollen and the ones obtained from regular pollen. While the average germination rate obtained from the regular pollen was approximately 72% none of the seeds obtained from artificial pollination with irradiated pollen germinated (p value of 2.43E-05).
The results are summarized in Table 14, below.

TABLE 14

| Sample | Germination Rate (%) |
|---|---|
| Regular pollen #1 | 73.33333 |
| Regular pollen #2 | 70 |
| Regular pollen #3 | 86.66667 |
| Regular pollen #4 | 56.66667 |
| Irradiated pollen #1 | 0 |
| Irradiated pollen #2 | 0 |
| Irradiated pollen #3 | 0 |
| Irradiated pollen #4 | 0 |
| Average value for regular pollen | 71.66667 |
| Average value for irradiated pollen | 0 |
| t-test p-value | 2.43E-05 |

The same experiment was conducted with an additional female plant in a similar manner only with 2 samples of X-ray irradiated pollen vs. 2 samples of non-irradiated pollen controls and a single "no-pollen" control. The results are depicted in Table 15 below.

TABLE 15

| Sample | Total Seed Weight (gr) | Number of Seeds | Average Seed Weight (mgr) |
|---|---|---|---|
| Regular pollen #1 | 0.0486 | 247 | 0.197 |
| Regular pollen #2 | 0.0401 | 202 | 0.199 |
| Irradiated pollen #1 | 0.0192 | 173 | 0.110 |
| Irradiated pollen #2 | 0.0138 | 170 | 0.081 |
| No-pollen | 0.0065 | 5 | NA |

TABLE 15-continued

| Sample | Total Seed Weight (gr) | Number of Seeds | Average Seed Weight (mgr) |
|---|---|---|---|
| Average value for regular pollen | 0.04435 | 224.5 | 0.198 |
| Average value for irradiated pollen | 0.0165 | 171.5 | 0.096 |
| t-test p-value | 0.031 | 0.143 | 0.020932284 |

Figures 3, 4:
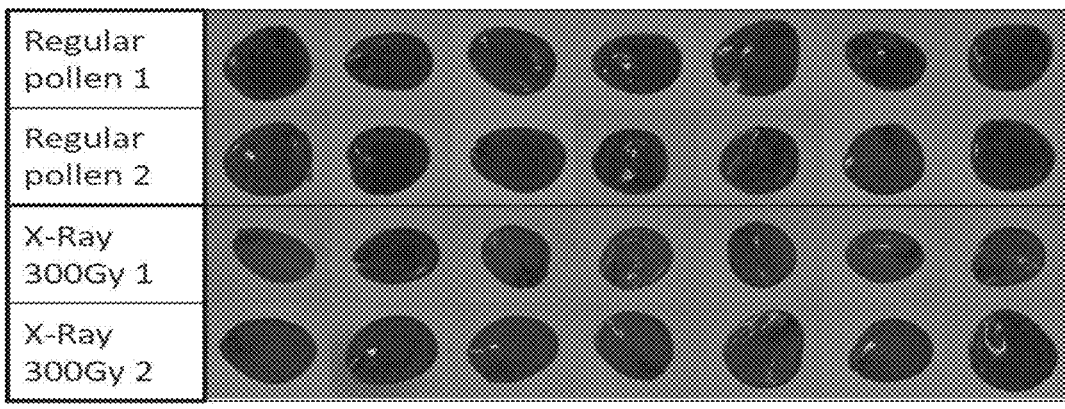
FIG. 3 is an image showing inhibition of seed development demonstrated by comparing the appearance of random assortment of seeds generated by artificial pollination with X-ray irradiated pollen vs. non-irradiated pollen.
FIG. 4 is an image showing inhibition of seed development demonstrated by comparing the appearance of random assortment of seeds generated by artificial pollination with gamma irradiated pollen vs. non-irradiated pollen. A dose response is demonstrated.

Seeds were examined under the microscope and for each sample pictures were taken for a random assortment of seeds with representative appearance (See FIG. 3). In general, the seeds obtained from the artificial pollination with the irradiated pollen looked thinner, partly empty and their color was lighter brown relative to the ones obtained from the regular pollen, which looked more filled, having a darker brown/black color.

A germination test was conducted as described above. The germination rates obtained are provided in Table 16 below.

TABLE 16

| Sample | Germination Rate (%) |
|---|---|
| Regular pollen #1 | 56.66667 |
| Regular pollen #2 | 16.66667 |
| Irradiated pollen #1 | 0 |
| Irradiated pollen #2 | 0 |
| Average value for regular pollen | 36.66667 |
| Average value for irradiated pollen | 0 |
| t-test p-value | 0.21 |

Overall, the results indicate that upon application of X-ray irradiated pollen, the seeds that are formed display seed development arrest with reduced number, weight and altered morphology and furthermore these seeds are devoid of their ability to germinate.

Example 25

Evaluation of *A. palmeri* Weed Control Efficiency by Artificial Pollination with UV Irradiated Pollen in Growth Room

*A. palmeri* seeds were germinated on paper and the seedlings were transferred into small pots. After the plants reached a height of about 20 cm they were transferred into larger pots. When plants began flowering, they were closely monitored daily to identify their sex at an early stage. Immediately after sex identification the females and males were separated and placed in different growth rooms in order to avoid pollination. One female plant with relatively many flowering spikes was transferred into a growth chamber (conditions of 34°/25° C., photoperiod 16/8 day/night) where the pollination experiment was conducted.

Pollen was collected at early morning from *A. palmeri* male plants using paper tubes (10 cm in length and diameter of ~1 cm). Each such paper tube was placed on a single male spike. Pollen was released by gently tapping on the paper tube. Six such paper tubes with fresh pollen were collected and divided into two sets of 3. Each set of 3 paper tubes was placed in a 15 cm petri dish. Each such paper tube was cut and opened carefully and was organized and placed with pollen exposed from the upper direction. One petri dish was put into UVITEC cross-linker machine for irradiation by UV-C (wave length of 254 nm) with energy of 2 joules. Total radiation time was 10 minutes. During this time the other petri dish was placed in similar conditions only without the irradiation treatment. After the irradiation procedure ended the opened paper tubes were re-attached to a cylindrical shape and each one of them was used to pollinate an *A.*

*palmeri* female spike (in total 6 spikes) by placing it (with the pollen inside) on one spike and gently tapping it (tapping procedure was repeated several times in intervals of ~15 minutes to enhance pollination). These 6 female spikes were originally divided into 3 pairs where the height of the branch origin of each such pair was approximately the same and pollination was conducted such that one spike from each pair was pollinated with the irradiated pollen and the other with non-irradiated pollen (overall 3 pairs were pollinated). The paper tubes were removed from the spikes after about an hour. 17 days after pollination, the top 10 cm of each of the 6 pollinated spikes plus additional 2 non-artificially pollinated spikes (that served as a "no-pollen" control) were cut and seeds were harvested. Total seed weight and total seed count per spike were measured and the results are depicted in Table 17 below.

TABLE 17

| Sample | Total Seed Weight (gr) | Number of Seeds | Average Seed Weight (gr) |
|---|---|---|---|
| Regular pollen #1 | 0.0506 | 157 | 0.000322 |
| Regular pollen #2 | 0.0927 | 263 | 0.000352 |
| Regular pollen #3 | 0.0447 | 108 | 0.000414 |
| Irradiated pollen #1 | 0.0078 | 12 | 0.00065 |
| Irradiated pollen #2 | 0.0315 | 48 | 0.000656 |
| Irradiated pollen #3 | 0.0053 | 7 | 0.000757 |
| No-pollen | 0 | 0 | |
| No-pollen | 0 | 0 | |
| Average value for regular pollen | 0.062666667 | 176 | |
| Average value for irradiated pollen | 0.014866667 | 22.33333 | |
| t-test p-value | 0.050404957 | 0.031884 | |

Overall, the results indicate that upon application of UV irradiated pollen a reduction in the number of seeds obtained is demonstrated compared to application of regular pollen.

Example 26

Evaluation of *A. palmeri* Weed Control Efficiency by Artificial Pollination with Gamma Irradiated Pollen in Growth Room The experiment was conducted similar to Example 24 (X-ray) with the difference that the pollen is irradiated by gamma irradiation with the following radiation intensities: 100, 300 and 500 Gy and compared to regular (non-irradiated) pollen as a control. The size of the paper tubes that were used for pollen collection and for artificial pollination was 6 cm in length. 4 paper tubes were used for each condition: non-irradiated pollen, 100 Gy, 300 Gy and 500 Gy. Additionally, 3 empty paper tubes were used in order to estimate the background level of seed production without pollination. 16 days after the artificial pollination stage, the pollinated spikes were cut and seeds were harvested. In order to evaluate the efficiency of the treatments, total seed weight, seed number and average weight per seed in each sample were measured and the average values for each treatment were compared.

The results are depicted in Table 18, below.

TABLE 18

| Sample | Total Seed Weight (gr) | Number of Seeds | Average Seed Weight (mgr) |
|---|---|---|---|
| Regular pollen #1 | 8.27E−02 | 231 | 3.58E−01 |
| Regular pollen #2 | 6.03E−02 | 212 | 2.84E−01 |
| Regular pollen #3 | 7.98E−02 | 234 | 3.41E−01 |

TABLE 18-continued

| Sample | Total Seed Weight (gr) | Number of Seeds | Average Seed Weight (mgr) |
|---|---|---|---|
| Regular pollen #4 | 6.82E–02 | 219 | 3.11E–01 |
| Irradiated pollen (100 Gy) #1 | 6.64E–02 | 231 | 2.87E–01 |
| Irradiated pollen (100 Gy) #2 | 7.51E–02 | 270 | 2.78E–01 |
| Irradiated pollen (100 Gy) #3 | 8.84E–02 | 291 | 3.04E–01 |
| Irradiated pollen (100 Gy) #4 | 3.29E–02 | 107 | 3.07E–01 |
| Irradiated pollen (300 Gy) #1 | 2.91E–02 | 157 | 1.85E–01 |
| Irradiated pollen (300 Gy) #2 | 3.72E–02 | 241 | 1.54E–01 |
| Irradiated pollen (300 Gy) #3 | 2.74E–02 | 183 | 1.50E–01 |
| Irradiated pollen (300 Gy) #4 | 3.18E–02 | 246 | 1.29E–01 |
| Irradiated pollen (500 Gy) #1 | 1.35E–02 | 96 | 1.41E–01 |
| Irradiated pollen (500 Gy) #2 | 6.90E–03 | 80 | 8.63E–02 |
| Irradiated pollen (500 Gy) #3 | 7.90E–03 | 106 | 7.45E–02 |
| Irradiated pollen (500 Gy) #4 | 4.90E–03 | 120 | 4.08E–02 |
| No-pollen # 1 | — | 2 | — |
| No-pollen # 2 | — | 6 | — |
| No-pollen # 3 | — | 14 | — |
| Average value for regular pollen | 7.27E–02 | 224 | 0.32 |
| Average value for irradiated pollen (100 Gy) | 6.57E–02 | 224.75 | 0.29 |
| Average value for irradiated pollen (300 Gy) | 3.13E–02 | 206.75 | 0.15 |
| Average value for irradiated pollen (500 Gy) | 8.30E–03 | 100.5 | 0.09 |
| t-test p-value (100 Gy versus regular pollen) | 6.05E–01 | 9.86E–01 | 1.45E–01 |
| t-test p-value (300 Gy versus regular pollen) | 3.17E–04* | 4.72E–01 | 1.45E–04* |
| t-test p-value (500 Gy versus regular pollen) | 2.34E–05* | 1.59E–05* | 1.02E–04* |

*P-value < 0.001

The data in the table demonstrates a significant decrease in total seed weight and weight per seed following pollination with the gamma irradiated pollen (300Gy and 500Gy) relatively to the ones obtained by regular pollen. In addition, seed number was also decreased significantly following the 500Gy irradiation treatment.

In addition, seed morphology was examined and compared to evaluate seed development. To that end seeds were examined under the microscope and for each sample pictures were taken for a random assortment of seeds with representative appearance (See FIG. 4). In general, the seeds obtained from the artificial pollination with the irradiated pollen looked thinner, partly empty and their color was lighter relative to the ones obtained from the regular pollen, which looked more filled, having a black color.

An additional repeat was conducted on a separate plant with conditions of regular (non-irradiated) pollen, 100 Gy and 300 Gy with one sample for each. It yielded a very similar trend. As shown in Table 19 below and in FIG. 5:

TABLE 19

| Sample | Total Seed Weight (gr) | Number of Seeds | Average Seed Weight (mgr) |
|---|---|---|---|
| Regular pollen | 1.23E–01 | 229 | 5.39E–01 |
| Irradiated pollen (100 Gy) | 1.74E–01 | 337 | 5.16E–01 |
| Irradiated pollen (300 Gy) | 5.56E–02 | 259 | 2.14E–01 |
| No-pollen # 1 | — | 0 | — |

Overall, the results indicate that upon application of gamma irradiated pollen, the seeds that are formed display seed development arrest with reduced number, weight and altered morphology.

Example 27

Evaluation of *A. palmeri* Weed Control Efficiency by Artificial Pollination with Chromosomally Aberrant Pollen in Growth Room

*A. palmeri* Seeds are germinated for 8 hours at a temperature of 34° C. in distilled water. Thereafter seeds are soaked in solutions with 3 different colchicine concentrations: 0.1%, 0.5% 1% with or without the addition of 1% DMSO. (Chen et al., 2004, Castro et al., 2003, Soo Jeong Kwon et al., 2014, Roselaine Cristina Pereiral et al.,). The soaking procedure is conducted for 4 or 20 hours at 34° C. Finally, the seeds are washed and seeded in a 6 cm petri dish on a towel paper with 7.5 ml tap water. The petri dishes are sealed with parafilm and are placed in a growth chamber at 34/25° C. 16/8h day/night conditions. One week later, seedlings are transferred into germination beds. Samples are taken to evaluate their chromosome set. The plants are then grown until reaching the flowering stage. Male plants with various chromosomal abnormalities (e.g., polyploidy, tertraploidy) are selected for an additional examination. Pollen is collected from these plants and tested for its ability to germinate in-vitro and to fertilize. Selected pollen is applied onto *A. palmeri* diploid female plants. Total seed weight, seed number, seed morphology and seed germination are examined in comparison to seeds obtained from pollination with regular diploid pollen as explained in Examples 24-26.

Example 28

Achieving Reduction of *A. palmeri* or *A. tuberculatus* Population by Application of Sterile Pollen in Controlled Field Conditions Sterile pollen is generated as described in Example 17, 18, 19 24, 25, 26 or 27 and collected as described in Example 1. Experiment is conducted similarly to Example 16 to evaluate weed control efficiency.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES (Other References are Cited in the Application)

1. Schnable and Wise. (1998). The molecular basis of cytoplasmic male sterility and fertility restoration. Trends in Plant Science. 3, 175-180.
2. Oerke, E-C. (2006) Crop losses to pests. J Agric. Sci. 144, 31-43

3. Pimentel, D. et al. (2000) Environmental and economic costs of nonindigenous species in the United States. BioScience 50,53-65

4. Delye et al. (2013) Deciphering the evolution of herbicide resistance in weeds. Trends in Genetics 29, 649-658

5. Klassen, W., C. F. Curtis (2005). History of the sterile insect technique, pp. 3-36 In V. A. Dyck, J. Hendrichs, and A. S. Robinson. The Sterile Insect Technique: Principles and Practice in Area-Wide Integrated Pest Management. Springer, Dordrecht, The Netherlands. 787 pp.

6. Yosiaki I T O et al. (2003) Eradication of the Melon Fly, Bactroceracucurbitae, from Okinawa, Japan, by Means of the Sterile Insect Technique, with Special Emphasis on the Role of Basic Studies, Journal of Asia-Pacific Entomology. 6, 119-129.

7. Kohama, T et al. (2003) A progress report on the eradication program of the sweet potato weevil, Cylasformicarius (Fabricius) (Coleoptera: Brentidae), with both male annihilation using sex pheromone and sterile insect releases in Kume Island, Okinawa, Japan, pp. 65-69. In Recent trends on sterile insect technique and area-wide integrated pest management—economic feasibility, control projects, farmer organization and Bactrocera *dorsalis* complex control study. Research Institute for Subtropics, Okinawa, Japan.

8. Pandey et al. (2006) Zinc is critically required for pollen function and fertilisation in lentil. Journal of Trace Elements in Medicine and BiologyVolume 20, Issue 2, Pages 89-96

9. Bhalla et al. (2001) Reduction in allergenicity of grass pollen by genetic engineering. Int Arch Allergy Immunol. 124 (1-3): 51-4.

10. Sauer, J. D. (1972) The dioecious amaranths: a new species name and major range extensions. Madrono 21:426-434.

11. Ribeiro, D. N. et al. (2012) Apomixis involvement in inheritance of glyphosate resistance in *Amaranthus palmeri* from Mississippi. Abstracts of the Weed Science Society of America Annual Meeting. www(dot)wssaabstracts(dot)com/public/9/abstract-438(dot)html.

12. Schernthaner, J. P. et al. (2003) Control of seed germination in transgenic plants based on the segregation of a two-component genetic system. PNAS 100 (11): 6855-6859.

13. Gaines, T. A et al. (2012) Interspecific hybridization transfers a previously unknown glyphosate resistance mechanism in *Amaranthus* species. Evolutionary Applications 5 (1): 29-38.

14. Padidam et al. (2003) Chemically regulated gene expression in plants. Curr Opin Plant Biol. 6 (2): 169-77.

15. Hughes, D. W., and Galau, G. A. (1989) Temporally modular gene expression during cotyledon development, Genes and Development 3:358-369.

16. Horak M J et al. (1997) Control and cross-resistance of an acetolactate synthase inhibitor-resistant palmer amaranth (*Amaranthus palmeri*) biotype Weed Technology 11 (1): p132

17. Patzoldt W L et al (2002). Variable herbicide response among Illinois waterhemp (*Amaranthus rudis* and *A. tuberculatus*) populations. Crop Prot 21:707-712

18. Culpepper A S et al. (2006). Glyphosate-resistant Palmer amaranth (*Amaranthus palmeri*) confirmed in Georgia. Weed Science 54 (4): 620-626.

19. Agriculture Research Service National Plant Germplasm System plant introduction 20. Vijay K. et al. (2013) Glyphosate Resistance in Tall Waterhemp (*Amaranthus tuberculatus*) from Mississippi is due to both Altered Target-Site and Nontarget-Site Mechanisms. Weed Science 61 (3): 374-383.

21. Heap, I. The International Survey of Herbicide Resistant Weeds.

22. Matzrafi M and Baruch R (2015) Multiple herbicide resistance in rigid ryegrass (*Lolium Rigidum*) in Israel. The 6th international weed science congress.

23. Khraiwesh, B. et al. (2012) Role of miRNAs and siRNAs in biotic and abiotic stress responses of plants. Biochim Biophys Acta. 1819 (2): 137-148

24. Santos-Mendoza et al., (2008) Deciphering gene regulatory networks that control seed development and maturation in *Arabidopsis*.

25. Pedrosa A M, et al., (2015) Late Embryogenesis Abundant (LEA) Constitutes a Large and Diverse Family of Proteins Involved in Development and Abiotic Stress Responses in Sweet Orange (*Citrus sinensis* L. Osb). 10(12).e0145785

26. Le B H et al., (2010) Global analysis of gene activity during *Arabidopsis* seed development and identification of seed-specific transcription factors. PNAS 26 107 (18) 8063-8070.

27. McElver J et al., (2001) Insertional Mutagenesis of Genes Required for Seed Development in *Arabidopsis thaliana*. Genetics 159:1751-1763.

28. Chen F, Bradford K J (2000) Expression of an expansin is associated with endosperm weakening during tomato seed germination. Plant Physiol. 124:1265-1274.

29. Nonogaki H, Gee O H, Bradford K J: A germination-specific endo mannanase gene is expressed in the micropylar endosperm cap of tomato seeds. Plant Physiol 2000, 123:1235-1246.

30. Leubner-Metzger G, Meins F: Sense transformation reveals a novel role for class I β-1,3-glucanase in tobacco seed germination. Plant J 2000, 23:215-221. A functional analysis of the role of 1,3 glucanases in seed germination.

31. Wu C T, Leubner-Metzger G, Meins F, Bradford K J: Class I β-1,3, -glucanase and chitinase are expressed in the micropylar endosperm of tomato seeds prior to radicle emergence. Plant Physiol 2001, 126:1299-1313.

32. Toorop P E, van Aelst A C, Hilhorst H W M: The second step of the biphasic endosperm cap weakening that mediates tomato (*Lycopersicon esculentum*) seed germination is under control of ABA. J Exp Bot 2000, 51:1371-1379.

33. Dubreucq B, Berger N, Vincent E, Boisson M, Pettetier G, •Caboche M, Lepiniec L: The *Arabidopsis* AtERP1 extensin-like gene is specifically expressed in endosperm during seed germination. Plant J 2000, 23:643-652.

34. Shu K et al. (2015) Dormancy and germination: How does the crop seed decide? Plant Biol 1104-1112:(6)17.

35. Jofre-Garfias, A E et al., (1997) *Agrobacterium*-mediated transformation of *Amaranthus hypochondriacus*: light- and tissue-specific expression of a pea chlorophyll a/b-binding protein promoter. Plant Cell Rep. 16, 847-852.

36. Swain et al., (2010) *Agrobacterium*× plant factors influencing transformation of 'Joseph's coat' (*Amaranthus tricolor* L.) Scientia Horticulturae 125:461-468.

37. Pal A. et al. (2013) *Agrobacterium* pRi TL-DNA rolB and TR-DNA Opine Genes Transferred to the Spiny Amaranth (*Amaranthus spinosus* L.), A Nutraceutical Crop, Food Technol. Biotechnol. 51 26-35.

38. Atkinson, N J and Urwin, P E (2012) The interaction of plant biotic and abiotic stresses: from genes to the field. J Exp Bot. 63 (10): 3523-3543.

39. Chen et al., (2004) The development of an *Arabidopsis* model system for genomewide analysis of polyploidy effects. Biol J Linn Soc Lond.; 82 (4): 689-700.

40. Castro et al., (2003) Changes in allele frequencies in colchicines-treated ryegrass populations assessed with RAPD markers. Agrociencia 9:107-112.
41. Soo Jeong Kwon et al., (2014) Tetraploid induction approach induced by colchicine of *Prunella vulgaris* for. albiflora Nakai. International Journal of Scientific and Research Publications, Volume 4, Issue 12, ISSN 2250-3153
42. Roselaine Cristina Pereira et al., (2014) Chromosome duplication in *Lolium multiflorum* Lam. Crop Breeding and Applied Biotechnology 14:251-255
Terminator patent—U.S. Pat. No. 5,723,765
Reverse sterility patents—AU621195, U.S. Pat. No. 5,808, 034

What is claimed is:

1. A method of producing pollen for use in weed control, the method comprising treating pollen of a weed species of interest selected from the group consisting of *Amaranthus tuberculatus* and *Amaranthus palmeri* with an effective amount of X-ray radiation or gamma radiation, which results in irradiated pollen that reduces productiveness of plants of said weed species of interest upon pollination with said irradiated pollen as compared to plants of said weed species of interest pollinated with control pollen not being treated with said effective amount of X-ray radiation or gamma radiation, wherein reduction in said productiveness is by:

(i) inability to develop an embryo;
(ii) embryo abortion;
(iii) seed that is unable to germinate; and/or
(iv) reduced or no seed set.

2. The method of claim 1 comprising harvesting pollen from the weed species of interest prior to or following said treating.

3. A method of producing pollen for use in artificial pollination, the method comprising:

(a) obtaining pollen according to the method of claim 1; and
(b) treating said pollen for use in artificial pollination.

* * * * *